(12) United States Patent
Singh et al.

(10) Patent No.: US 8,992,458 B2
(45) Date of Patent: Mar. 31, 2015

(54) SYSTEMS AND METHODS FOR REDUCING OR PREVENTING BACKFLOW IN A DELIVERY SYSTEM

(71) Applicant: Alcyone Lifesciences, Inc., Concord, MA (US)

(72) Inventors: Deep Arjun Singh, Allston, MA (US); PJ Anand, Ayer, MA (US)

(73) Assignee: Alcyone Lifesciences, Inc., Concord, MA (US)

( * ) Notice: Subject to any disclaimer, the term of this patent is extended or adjusted under 35 U.S.C. 154(b) by 0 days.

(21) Appl. No.: 14/132,762

(22) Filed: Dec. 18, 2013

(65) Prior Publication Data

US 2014/0171760 A1 Jun. 19, 2014

Related U.S. Application Data

(60) Provisional application No. 61/835,912, filed on Jun. 17, 2013, provisional application No. 61/738,850, filed on Dec. 18, 2012.

(51) Int. Cl.
*A61N 1/30* (2006.01)
*A61M 25/00* (2006.01)
(Continued)

(52) U.S. Cl.
CPC ....... *A61M 25/0071* (2013.01); *A61M 25/0068* (2013.01); *A61M 25/001* (2013.01);
(Continued)

(58) Field of Classification Search
CPC ................. A61M 25/0071; A61M 2025/0042; A61M 2025/0073; A61M 2037/003
USPC ............ 604/115, 117, 196, 19, 20, 39, 43, 44
See application file for complete search history.

(56) References Cited

U.S. PATENT DOCUMENTS 3,460,537 A 8/1969 Zeis
4,917,686 A 4/1990 Bayston et al.
(Continued)

FOREIGN PATENT DOCUMENTS

WO 95/05864 A1 3/1995
WO 97/40874 A1 11/1997
(Continued)

OTHER PUBLICATIONS

Burmeister et al.; Improved Ceramic-Based Multisite Microelectrode for Rapid Measurements of L-Giutamate in the CNS; Journal of Neuroscience Methods 119 (2002) 163-171; Elsevier Science B.V.
(Continued)

*Primary Examiner* — Kami A Bosworth
(74) *Attorney, Agent, or Firm* — Nutter McClennen & Fish LLP

(57) ABSTRACT

Systems and methods are disclosed herein that generally involve CED devices with various features for reducing or preventing backflow. In some embodiments, CED devices include a tissue-receiving space disposed proximal to a distal fluid outlet. Tissue can be compressed into or pinched/pinned by the tissue-receiving space as the device is inserted into a target region of a patient, thereby forming a seal that reduces or prevents proximal backflow of fluid ejected from the outlet beyond the tissue-receiving space. In some embodiments, CED devices include a bullet-shaped nose proximal to a distal fluid outlet. The bullet-shaped nose forms a good seal with surrounding tissue and helps reduce or prevent backflow of infused fluid.

27 Claims, 18 Drawing Sheets

(51) Int. Cl.
*A61M 5/168* (2006.01)
*A61M 37/00* (2006.01)

(52) U.S. Cl.
CPC .. *A61M2037/003* (2013.01); *A61M 2025/0042* (2013.01); *A61M 5/16813* (2013.01); *A61M 2025/0073* (2013.01)
USPC .......................................................... 604/19

(56) References Cited

U.S. PATENT DOCUMENTS

| | | | |
|---|---|---|---|
| 4,979,284 | A | 12/1990 | McMurtry et al. |
| 5,088,208 | A | 2/1992 | Wells et al. |
| 5,101,548 | A | 4/1992 | McMurtry et al. |
| 5,415,648 | A * | 5/1995 | Malay et al. ................ 604/181 |
| 5,509,910 | A | 4/1996 | Lunn |
| 5,590,657 | A | 1/1997 | Cain et al. |
| 5,620,479 | A | 4/1997 | Diederich |
| 5,720,720 | A | 2/1998 | Laske et al. |
| 6,176,842 | B1 | 1/2001 | Tachibana et al. |
| 6,309,634 | B1 | 10/2001 | Bankiewicz et al. |
| 6,454,945 | B1 | 9/2002 | Weigl et al. |
| 6,464,662 | B1 | 10/2002 | Raghavan et al. |
| 6,599,274 | B1 | 7/2003 | Kucharczyk et al. |
| 6,626,902 | B1 | 9/2003 | Kucharczyk et al. |
| 6,953,575 | B2 | 10/2005 | Bankiewicz et al. |
| 7,029,697 | B2 | 4/2006 | Segura et al. |
| 7,048,716 | B1 | 5/2006 | Kucharczyk et al. |
| 7,316,676 | B2 * | 1/2008 | Peyman et al. ................ 604/521 |
| 7,534,613 | B2 | 5/2009 | Bankiewicz et al. |
| 7,588,574 | B2 | 9/2009 | Assell et al. |
| 7,984,929 | B2 | 7/2011 | Gill |
| 8,128,600 | B2 | 3/2012 | Gill |
| 8,309,355 | B2 | 11/2012 | Bankiewicz et al. |
| 8,790,317 | B2 | 7/2014 | Olbricht et al. |
| 2001/0005552 | A1 | 6/2001 | Berg et al. |
| 2002/0055731 | A1 | 5/2002 | Atala et al. |
| 2002/0099356 | A1 | 7/2002 | Unger et al. |
| 2002/0138036 | A1 | 9/2002 | Babaev |
| 2003/0048969 | A1 | 3/2003 | Hunter et al. |
| 2003/0138403 | A1 | 7/2003 | Drustrup |
| 2003/0205947 | A1 | 11/2003 | Klee et al. |
| 2003/0216714 | A1 | 11/2003 | Gill |
| 2004/0073114 | A1 | 4/2004 | Oliver et al. |
| 2004/0260241 | A1 * | 12/2004 | Yamamoto et al. ........... 604/117 |
| 2005/0125007 | A1 | 6/2005 | Gill |
| 2005/0137134 | A1 | 6/2005 | Gill et al. |
| 2005/0137531 | A1 | 6/2005 | Prausnitz et al. |
| 2005/0154297 | A1 | 7/2005 | Gill |
| 2005/0190999 | A1 | 9/2005 | Hunter et al. |
| 2005/0236566 | A1 | 10/2005 | Liu |
| 2005/0277862 | A1 | 12/2005 | Anand |
| 2006/0003310 | A1 | 1/2006 | Klauke et al. |
| 2006/0025752 | A1 | 2/2006 | Broaddus et al. |
| 2007/0055180 | A1 | 3/2007 | Deem et al. |
| 2007/0088295 | A1 | 4/2007 | Bankiewicz |
| 2007/0123843 | A1 | 5/2007 | Gill |
| 2007/0163137 | A1 | 7/2007 | Hunter et al. |
| 2007/0276340 | A1 | 11/2007 | Poston et al. |
| 2008/0004572 | A1 | 1/2008 | Morris et al. |
| 2008/0275466 | A1 | 11/2008 | Skakoon |
| 2008/0294096 | A1 * | 11/2008 | Uber et al. ........................ 604/66 |
| 2009/0030373 | A1 | 1/2009 | Gill |
| 2009/0048508 | A1 | 2/2009 | Gill et al. |
| 2009/0124976 | A1 | 5/2009 | Mittermeyer |
| 2009/0143764 | A1 | 6/2009 | Nelson |
| 2009/0198218 | A1 | 8/2009 | Gill et al. |
| 2009/0224529 | A1 | 9/2009 | Gill |
| 2009/0279815 | A1 | 11/2009 | Hunter et al. |
| 2009/0304314 | A1 | 12/2009 | Derrick et al. |
| 2010/0030148 | A1 * | 2/2010 | Alchas et al. ................. 604/115 |
| 2010/0042070 | A1 | 2/2010 | Gill et al. |
| 2010/0042098 | A1 | 2/2010 | Cross et al. |
| 2010/0098767 | A1 | 4/2010 | Olbricht et al. |
| 2010/0130884 | A1 | 5/2010 | Linninger |
| 2010/0217228 | A1 | 8/2010 | Grahn et al. |
| 2010/0217236 | A1 | 8/2010 | Gill et al. |
| 2010/0312193 | A1 | 12/2010 | Stratton et al. |
| 2010/0318061 | A1 | 12/2010 | Derrick et al. |
| 2010/0318064 | A1 | 12/2010 | Derrick et al. |
| 2011/0009879 | A1 | 1/2011 | Derrick et al. |
| 2011/0137289 | A1 | 6/2011 | Kunst |
| 2011/0200244 | A1 | 8/2011 | Ashton et al. |
| 2011/0282319 | A1 | 11/2011 | Gill |
| 2011/0301235 | A1 | 12/2011 | Erlanson et al. |
| 2012/0046666 | A1 | 2/2012 | Klein |
| 2012/0060847 | A1 | 3/2012 | Stratton et al. |
| 2012/0065496 | A1 | 3/2012 | Stratton et al. |
| 2012/0083742 | A1 | 4/2012 | Nelson |
| 2012/0123391 | A1 | 5/2012 | Gill et al. |
| 2012/0257846 | A1 | 10/2012 | Derrick et al. |
| 2012/0302959 | A1 | 11/2012 | Fielder et al. |
| 2012/0310182 | A1 | 12/2012 | Fielder et al. |
| 2012/0310215 | A1 | 12/2012 | Stout et al. |
| 2013/0019488 | A1 | 1/2013 | Mcmurtry et al. |
| 2013/0035560 | A1 | 2/2013 | Anand et al. |
| 2013/0035574 | A1 | 2/2013 | Anand |
| 2013/0035660 | A1 | 2/2013 | Anand |
| 2013/0046230 | A1 | 2/2013 | Lewis, Jr. et al. |
| 2014/0171902 | A1 | 6/2014 | Singh et al. |
| 2014/0371711 | A1 | 12/2014 | Singh et al. |
| 2014/0371712 | A1 | 12/2014 | Olbricht et al. |

FOREIGN PATENT DOCUMENTS

| | | |
|---|---|---|
| WO | 97/48425 A2 | 12/1997 |
| WO | 98/52064 A1 | 11/1998 |
| WO | 99/52585 A1 | 10/1999 |
| WO | 00/51669 A1 | 9/2000 |
| WO | 02/068036 A1 | 9/2002 |
| WO | 02/085431 A2 | 10/2002 |
| WO | 2004/060465 A2 | 7/2004 |
| WO | 2006/015091 A2 | 2/2006 |
| WO | 2008/100930 A2 | 8/2008 |
| WO | 2010/006293 A2 | 1/2010 |
| WO | 2010/081072 A2 | 7/2010 |
| WO | 2011/109735 A2 | 9/2011 |
| WO | 2014/016591 A1 | 1/2014 |

OTHER PUBLICATIONS

International Search Report for International Application No. PCT/US2011/027238, dated Nov. 16, 2011.
International Search Report and Written Opinion for Application No. PCT/US2012/049100, issued Jan. 29, 2013. (12 pages).
International Search Report and Written Opinion for Application No. PCT/US2013/076084 mailed Mar. 11, 2014 (13 Pages).
Olbricht, William L. et al., Microfluidic Probes in the Treatment of Brain-Related Diseases, Drug News and Perspectives, 2010, 23(8)—7 pages (Oct. 2010).
Saltzman et al.; Building Drug Delivery Into Tissue Engineering; Nature Reviews/Drug Discovery; 2002 Macmillan Magazines Ltd.; vol. 1; Mar. 2002; pp. 177-186.
International Search Report and Written Opinion for Application No. PCT/US2014/042726 mailed Oct. 28, 2014 (13 Pages).
Invitation to Pay Additonal Fees for Application No. PCT/US2014/049031, mailed Nov. 24, 2014 (2 pages).
Lewis et al., Design and characterization of a high-power ultrasound driver with ultralow-output impedance. Rev Sci Instrum. Nov. 2009;80(11):114704.1-114704.8.

* cited by examiner

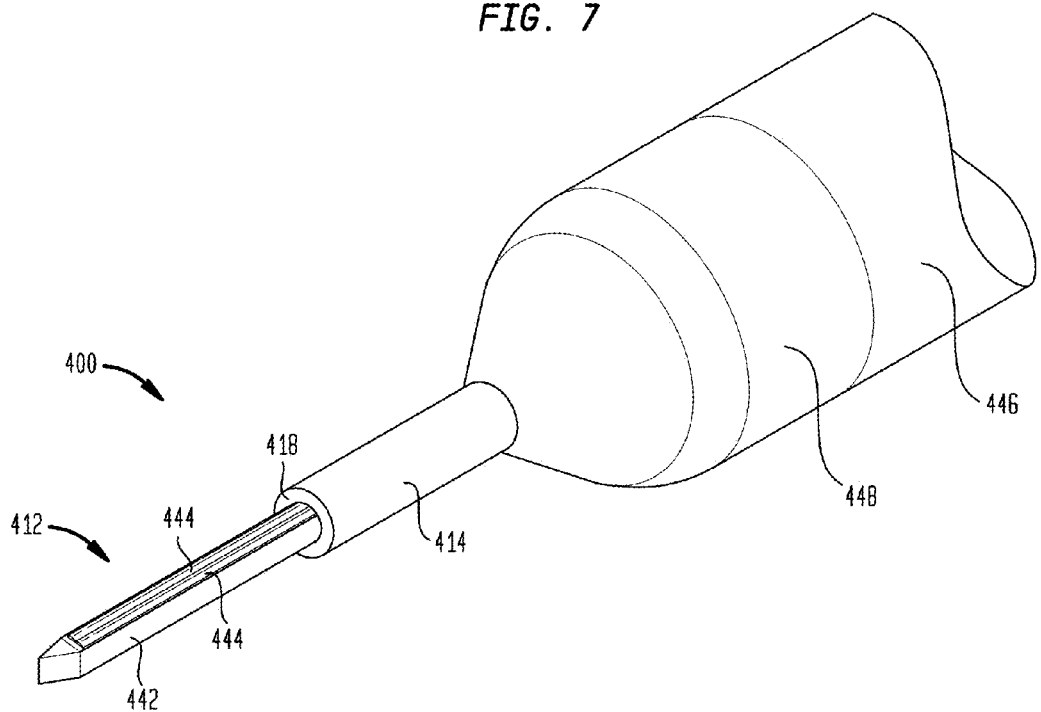
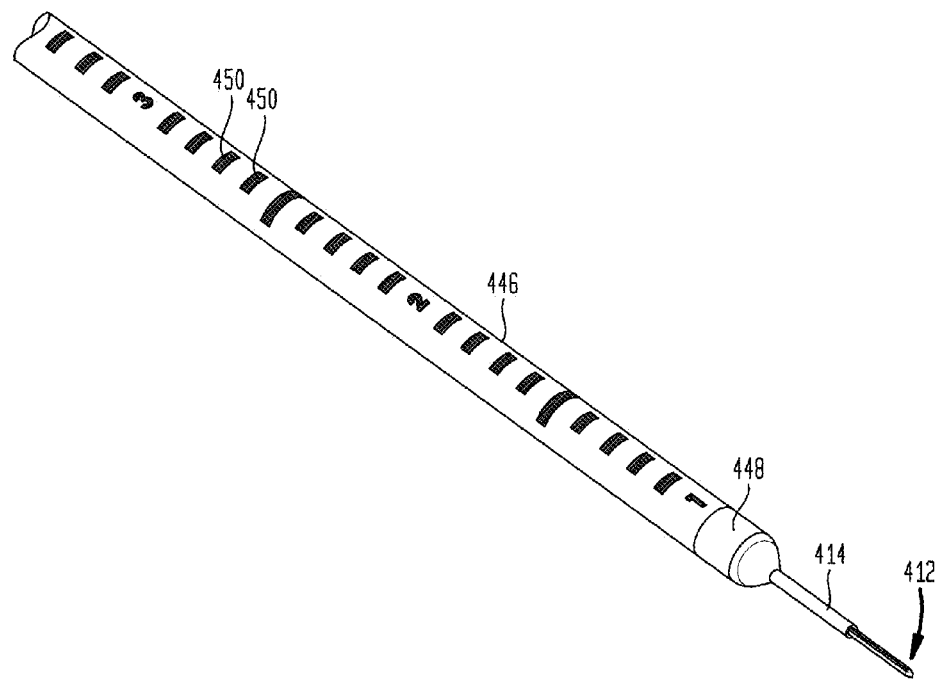

5 µL/min    10 µL/min    12 µL/min 5 mins    10 mins    45 mins

| FLOW RATE (μl/min) | 1 | 3 | 5 | 10 | 20 |

| FLOW RATE (μl/min) | 1 | 3 | 5 | 10 | 20 |

| FLOW RATE (μl/min) | 1 | 2 | 5 | 10 | 15 |

| TIME (min) | 1 | 9 | 16 | 24 | 50 |
|---|---|---|---|---|---|
| INFUSE (µl) | 5 | 45 | 80 | 120 | 160 |

SYSTEMS AND METHODS FOR REDUCING OR PREVENTING BACKFLOW IN A DELIVERY SYSTEM

CROSS-REFERENCE TO RELATED APPLICATIONS

This application claims priority to U.S. Provisional Application No. 61/738,850 filed on Dec. 18, 2012 and U.S. Provisional Application No. 61/835,912 filed on Jun. 17, 2013, which are each incorporated herein by reference in their entirety.

FIELD

The present invention relates to systems and methods for reducing or preventing backflow in delivery systems, such as convection-enhanced delivery systems for delivering therapeutic agents to a patient.

BACKGROUND

In convection-enhanced delivery (CED), drugs are infused locally into tissue through a needle, cannula, or microcatheter inserted into the tissue. Transport of the infused material is dominated by convection, which enhances drug penetration into the target tissue compared with diffusion-mediated delivery or systemic delivery.

CED has emerged as a leading investigational delivery technique for the treatment of several disorders. Clinical trials using existing devices show mixed results and suggest that the outcome of the therapy depends strongly on the extent of penetration and distribution of the drug into the target tissue, which is determined by infusion velocity, the relative rates of convection and elimination during CED, and various properties of the target tissue.

As infusion velocity increases, there can be a tendency for the infused fluid to flow back along the insertion pathway, between the exterior of the microcatheter and the surrounding tissue. Flexible microcatheter designs have been constructed to reduce this backflow of the drug-containing fluid. However, fluid backflow during CED treatment still remains a critical problem in clinical practice. This is particularly true in the case of CED within the brain, as the poroelastic nature of the brain tissue contributes to backflow or reflux. There is therefore a need for improved CED devices, e.g., CED devices that reduce or eliminate backflow of the infused fluid between the exterior of the device and the surrounding tissue.

SUMMARY

Systems and methods are disclosed herein that generally involve CED devices with various features for reducing or preventing backflow. In some embodiments, CED devices include a tissue-receiving space disposed proximal to a distal fluid outlet. Tissue can be compressed into or pinched/pinned by the tissue-receiving space as the device is inserted into a target region of a patient, thereby forming a seal that reduces or prevents proximal backflow of fluid ejected from the outlet beyond the tissue-receiving space. In some embodiments, CED devices include a bullet-shaped nose proximal to a distal fluid outlet. The bullet-shaped nose forms a good seal with surrounding tissue and helps reduce or prevent backflow of infused fluid.

In some embodiments, a convection-enhanced-delivery (CED) device is provided that includes a micro-tip having a proximal portion, a central portion, a distal portion, and at least one fluid channel extending along said proximal, central, and distal portions, the at least one fluid channel having an outlet port at a distal end thereof and an inlet port at a proximal end thereof. The device also includes a first outer sheath disposed coaxially over the distal portion of the micro-tip such that the distal portion of the micro-tip protrudes from a distal end of the first outer sheath, a first tissue-receiving space defined between an exterior surface of the micro-tip and an interior surface of the distal end of the first outer sheath, and a catheter body extending proximally from the micro-tip such that the at least one fluid channel of the micro-tip is in fluid communication with a respective inner lumen of the catheter body. The device also includes a nose portion disposed over at least the central portion of the micro-tip and extending between the first outer sheath and the catheter body such that the nose portion defines an exterior surface that tapers from a reduced distal diameter corresponding to the outside diameter of the first outer sheath to an enlarged proximal diameter corresponding to the outside diameter of the catheter body.

The tissue-receiving space can be configured to compress tissue received therein as the device is advanced through the tissue. Tissue compressed by the tissue-receiving space can form a seal that reduces proximal backflow of fluid ejected from the outlet port of the at least one fluid channel beyond the tissue-receiving space. The device can include a second outer sheath disposed over the first outer sheath such that a second tissue-receiving space is defined between an exterior surface of the first outer sheath and an interior surface of a distal end of the second outer sheath. The interior surface of the distal end of the first outer sheath can be shaped to compress tissue received therein as the device is advanced through the tissue. The interior surface of the distal end of the first outer sheath can be conical, convex, and/or concave.

An inside diameter of the distal end of the first outer sheath can be about 1 μm to about 200 μm greater than an outside diameter of the distal portion of the micro-tip. An inside diameter of the distal end of the first outer sheath can be about 10 percent to about 100 percent greater than an outside diameter of the distal portion of the micro-tip. The first outer sheath can have a circular outside cross-section. The at least one fluid channel can be formed from at least one of a parylene composition, a silastic composition, a polyurethane composition, and a PTFE composition. The device can include a fluid reservoir in fluid communication with the inner lumen of the catheter body and configured to supply a fluid thereto under positive pressure. The micro-tip can be flexible. The micro-tip can include an embedded microsensor.

The embedded microsensor can include at least one of an interrogatable sensor, a pressure sensor, a glutamate sensor, a pH sensor, a temperature sensor, an ion concentration sensor, a carbon dioxide sensor, an oxygen sensor, and a lactate sensor. The distal end of the micro-tip can have an atraumatic shape configured to penetrate tissue without causing trauma. The micro-tip can contain a quantity of a drug, can be coated with a drug, and/or can be impregnated with a drug. The drug can include at least one of an antibacterial agent, an anti-inflammatory agent, a corticosteroid, and dexamethasone. The micro-tip can include a substrate having the at least one fluid channel formed thereon. The substrate can have a rectangular transverse cross-section. The catheter body can be formed from a rigid material. Each inner lumen of the catheter body can be defined by a sleeve formed from a flexible material. The catheter body can be formed from at least one of ceramic, PEEK, and polyurethane. Each sleeve can be formed from at least one of polyimide, pebax, PEEK, polyurethane, silicone, and fused silica. The catheter body can be formed from a flexible material. The device can be assembled by forming the nose portion by molding the nose portion over the first outer sheath, inserting the micro-tip into a proximal end of the nose portion, coupling the proximal portion of the micro-tip to the catheter body, and injecting a flowable material through an inlet port formed in the nose portion to fill the interior of the nose portion and secure the micro-tip and catheter body to the nose portion.

In some embodiments, a convection-enhanced-delivery (CED) device is provided that includes a fluid conduit having proximal and distal ends, a first outer sheath disposed coaxially over the fluid conduit such that the fluid conduit extends out of a distal end of the first outer sheath, and a first tissue-receiving space defined between an exterior surface of the fluid conduit and an interior surface of the distal end of the first outer sheath.

In some embodiments, a micro-molding device is provided that includes a mold cavity sized and configured to receive a catheter body and a catheter micro-tip therein such that at least one fluid channel of the micro-tip is at least partially disposed within a corresponding fluid line of the catheter body. The device also includes one or more mold channels though which a mold fluid can be injected to fill the mold cavity and secure the micro-tip to the catheter body such that the at least one fluid channel of the micro-tip is in fluid communication with the at least one fluid line of the catheter body. The device can be transparent to allow UV light to pass therethrough to cure mold fluid disposed within the mold cavity. The mold cavity can be sized and configured to form a bullet nose portion over the micro-tip and over at least a portion of an outer sheath received in the mold cavity.

In some embodiments, a method of delivering a therapeutic agent to a patient is provided. The method includes advancing a fluid conduit having a first outer sheath disposed therearound into tissue to compress tissue into a first tissue-receiving space defined between an exterior surface of the fluid conduit and an interior surface of the distal end of the first outer sheath. The method also includes delivering fluid containing the therapeutic agent under positive pressure through the fluid conduit and into a portion of the tissue adjacent to a distal end of the fluid conduit.

The method can include delivering a sealing gel through the fluid conduit, before delivering the fluid containing the therapeutic agent, to fill one or more voids that exist between the fluid conduit and the tissue. Tissue compressed into the first tissue-receiving space can form a seal that reduces proximal backflow of fluid ejected from the distal end of the fluid conduit beyond the tissue-receiving space. The method can include advancing a second outer sheath disposed over the first outer sheath into the tissue such that tissue is compressed into a second tissue-receiving space defined between an exterior surface of the first outer sheath and an interior surface of the distal end of the second outer sheath. The interior surface of the distal end of the first outer sheath can be at least one of cylindrical, conical, convex, and concave. The method can include controlling delivery of fluid through the fluid conduit based on an output of a microsensor embedded in the fluid conduit. The method can be used to treat at least one condition selected from central-nervous-system (CNS) neoplasm, intractable epilepsy, Parkinson's disease, Huntington's disease, stroke, lysosomal storage disease, chronic brain injury, Alzheimer's disease, amyotrophic lateral sclerosis, balance disorders, hearing disorders, and cavernous malformations. Advancing the fluid conduit can include urging a nose portion into contact with tissue, the nose portion extending between the first outer sheath and a proximal catheter body such that the nose portion tapers from a reduced distal diameter corresponding to the outside diameter of the first outer sheath to an enlarged proximal diameter corresponding to the outside diameter of the catheter body. The fluid conduit can be coupled to a distal end of a flexible catheter and the method can include inserting the catheter through an incision, positioning the fluid conduit in proximity to the portion of the tissue using stereotactic targeting, removing a stylet inserted through the catheter, tunneling a proximal end of the catheter beneath the scalp of the patient, and coupling one or more proximal fluid connectors of the catheter to a fluid delivery system.

The present invention further provides devices, systems, and methods as claimed.

BRIEF DESCRIPTION OF THE DRAWINGS

The invention will be more fully understood from the following detailed description taken in conjunction with the accompanying drawings, in which:

FIG. 7 is a perspective view of another exemplary embodiment of a CED device;

FIG. 8 is another perspective view of the CED device of FIG. 7;

DETAILED DESCRIPTION

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Systems and methods are disclosed herein that generally involve CED devices with various features for reducing or preventing backflow. In some embodiments, CED devices include a tissue-receiving space disposed proximal to a distal fluid outlet. Tissue can be compressed into or pinched/pinned by the tissue-receiving space as the device is inserted into a target region of a patient, thereby forming a seal that reduces or prevents proximal backflow of fluid ejected from the outlet beyond the tissue-receiving space. In some embodiments, CED devices include a bullet-shaped nose proximal to a distal fluid outlet. The bullet-shaped nose forms a good seal with surrounding tissue and helps reduce or prevent backflow of infused fluid.

Figure 1:
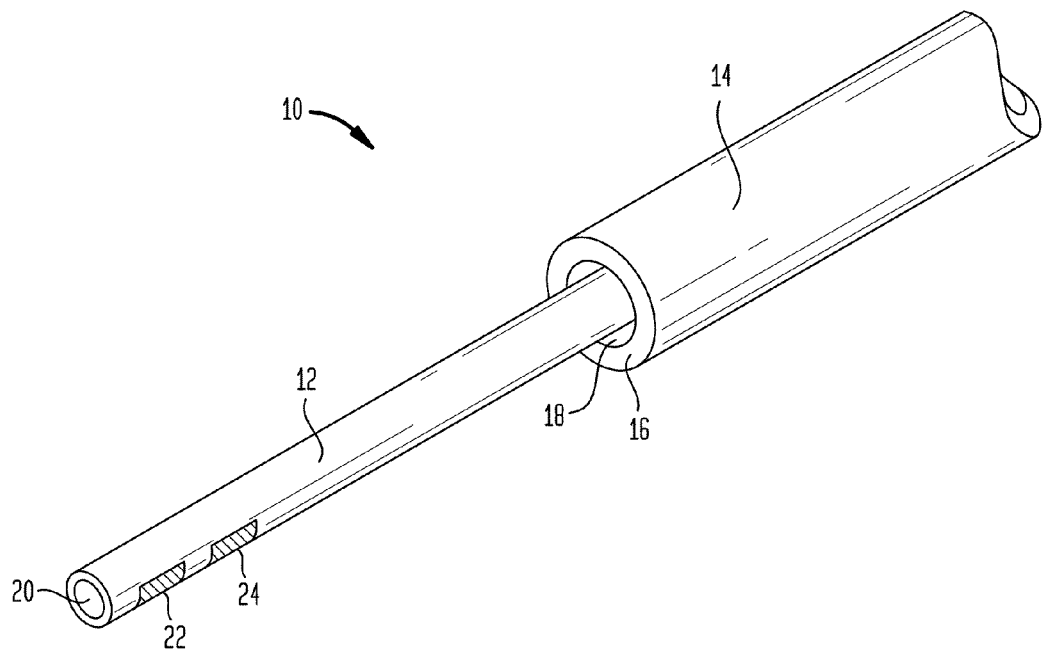
FIG. 1 is a perspective view of one exemplary embodiment of a CED device.

FIG. 1 illustrates one exemplary embodiment of a CED device 10. The device 10 generally includes a fluid conduit 12 and an outer sheath 14. The outer sheath 14 can be disposed coaxially over the fluid conduit 12 such that the fluid conduit 12 extends out of a distal end 16 of the outer sheath 14. The fluid conduit 12 and the outer sheath 14 can be sized and dimensioned such that a tissue-receiving space 18 is formed between an exterior surface of the fluid conduit 12 and an interior surface of the distal end 16 of the outer sheath 14.

The fluid conduit 12 can define one or more fluid lumens that extend generally parallel to the central longitudinal axis of the device 10. The fluid conduit 12 can include a fluid inlet port (not shown in FIG. 1) and a fluid outlet port 20. While a single fluid outlet port 20 is shown in the illustrated embodiment, it will be appreciated that the device can include a plurality of fluid outlet ports, as well as a plurality of fluid inlet ports and a plurality of fluid lumens extending therebetween. The fluid inlet port can be positioned at a proximal end of the device 10, and can allow the fluid conduit 12 to be placed in fluid communication with a fluid reservoir, e.g., via one or more catheters, pumps, meters, valves, or other suitable control devices. Such control devices can be used to regulate the pressure at which fluid is supplied to the device 10, or the rate or volume of fluid that is supplied to the device 10.

Fluid supplied to the conduit 12 though the fluid inlet port can be directed through one or more inner lumens of the conduit 12 and released through the one or more fluid outlet ports 20. The fluid outlet ports 20 can be sized, shaped, and/or positioned to control various release parameters of the fluid. For example, the fluid outlet ports 20 can be configured to control the direction in which fluid is released from the device 10, the distribution of the fluid within the target tissue, and the velocity or pressure at which the fluid is released. In exemplary embodiments, the size of the fluid outlet ports can progressively increase towards the distal end of the device 10, which can advantageously compensate for pressure loss that occurs along the length of the device such that fluid is released from each of the plurality of fluid outlet ports at substantially the same pressure. The fluid outlet ports can also be positioned at various points around the circumference of the fluid conduit 12 or can be shaped to control the release direction of the fluid.

The fluid conduit 12 and/or the outer sheath 14 can have circular outside cross-sections, which can advantageously allow the device 10 to rotate within the tissue without causing trauma or forming large gaps between the exterior of the device and the surrounding tissue that might increase backflow. The fluid conduit 12 can also be flexible to allow it to move with the tissue in which it is inserted. While a generally-cylindrical fluid conduit 12 is shown, the fluid conduit 12 can also have a non-cylindrical or polygonal cross-section. For example, as described below with respect to FIG. 7, the fluid conduit 12 can be a microfabricated tip that includes a substrate having a square or rectangular cross-section with one or more fluid channels disposed thereon. The interior of the outer sheath 14 can be shaped to substantially correspond to the cross-section of the fluid conduit 12. Alternatively, the outer sheath 14 can have an interior cross-sectional shape that differs from the exterior cross-sectional shape of the fluid conduit 12. For example, the outer sheath 14 can have a substantially cylindrical interior cross-sectional shape at its distal end, while the fluid conduit 12 can have a substantially square or rectangular exterior cross-sectional shape, thereby defining the tissue-receiving space 18 between the exterior of the fluid conduit 12 and the interior of the outer sheath 14.

Figure 2:
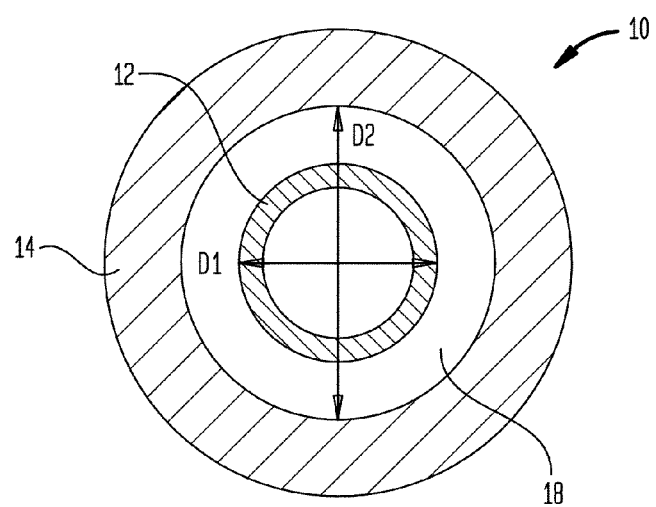
FIG. 2 is a cross-sectional view of the device of FIG. 1, taken in a plane normal to the longitudinal axis of the device.

As noted above, the outer sheath 14 can be disposed coaxially over the fluid conduit 12 such that the fluid conduit 12 extends out of the distal end 16 of the outer sheath 14. A clearance space between the exterior surface of the fluid conduit 12 and the interior surface of the sheath 14 can define the tissue-receiving space 18. For example, as shown in FIG. 2, the fluid conduit 12 can have an outside diameter D1 that is less than an inside diameter D2 of the outer sheath 14. The degree to which the diameter D2 exceeds the diameter D1 can dictate the amount of tissue that is compressed into or pinched by the tissue-receiving space 18.

In some embodiments, an adhesive or other filler can be disposed between the fluid conduit 12 and the sheath 14 to hold the fluid conduit in a fixed longitudinal position relative to the sheath and to maintain the fluid conduit in the center of the sheath (e.g., such that the tissue-receiving space 18 has a uniform width about the circumference of the fluid conduit). For example, the tissue-receiving space 18 can extend proximally a first distance from the distal end 16 of the sheath 14, after which point the clearance space between the fluid conduit 12 and the sheath 14 can be filled. In some embodiments, the sheath 14 can have a stepped, tapered, or other similarly-shaped interior such that a clearance space exists along a distal portion of the sheath 14 and no clearance space exists along a proximal portion of the sheath 14.

In exemplary embodiments, the inside diameter of the distal end 16 of the outer sheath 14 can be about 1 µm to about 1000 µm, about 1 µm to about 500 µm, about 1 µm to about 200 µm, or about 1 µm to about 20 µm greater than the outside diameter of the fluid conduit 12. In exemplary embodiments, the inside diameter of the distal end 16 of the outer sheath 14 can be about 5 percent to about 500 percent, about 5 percent to about 250 percent, about 10 percent to about 100 percent, or about 10 percent to about 20 percent greater than the outside diameter of the fluid conduit 12. In exemplary embodiments, the diameter D1 can be about 50 µm to about 2000 µm, about 50 µm to about 1000 µm, or about 50 µm to about 200 µm. In exemplary embodiments, diameter D2 can be about 51 µm to about 5000 µm, about 55 µm to about 1000 µm, or about 55 µm to about 200 µm. The tissue-receiving space 18 can extend along the entire length of the outer sheath 14, or along only a portion of the outer sheath (e.g., along about 1 mm to about 100 mm, about 1 mm to about 50 mm, or about 1 mm to about 10 mm of the distal-most portion of the outer sheath).

The fluid conduit 12 and the outer sheath 14 can be formed from any of a variety of materials, including parylene compositions, silastic compositions, polyurethane compositions, PTFE compositions, silicone compositions, and so forth.

In some embodiments, the device 10 can be mounted on a support scaffold (not shown) to provide structural rigidity to the device and facilitate insertion into the target tissue. Exemplary support scaffolds are illustrated and described in U.S. Publication No. 2013/0035560, filed on Aug. 1, 2012, entitled "MULTI-DIRECTIONAL MICROFLUIDIC DRUG DELIVERY DEVICE," the entire contents of which are incorporated herein by reference. To assist with tissue penetration and navigation, the distal end of the fluid conduit 12 and/or the distal end of the scaffold can be tapered, pointed, and/or sharpened. In some embodiments, the fluid conduit 12 and/or the scaffold can be provided with a rounded atraumatic tip so as to facilitate insertion through tissue without causing trauma to the tissue. The support scaffold can be rigid or semi-rigid and can be formed from a degradable thermoplastic polymer, for example, a degradable thermoplastic polyester or a degradable thermoplastic polycarbonate. In some embodiments, the support scaffold can be formed from poly (lactic-co-glycolic acid) (PLGA) and can be configured to biodegrade within the target tissue. This can advantageously eliminate the need to remove the support scaffold once the device 10 is positioned within target tissue, thereby avoiding the potential to disrupt the positioning of the fluid conduit 12. Any of a variety of other materials can also be used to form the support scaffold, including silicon or various ceramics, metals, and plastics known in the art. The scaffold can have a width of approximately 100 µm to approximately 200 µm and can have a length that varies depending on the target tissue (e.g., depending on the depth at which the target tissue is situated). In one embodiment, the scaffold is between 2 cm and 3 cm long. A variety of techniques can be used to couple the fluid conduit 12 and/or the outer sheath 14 to the support scaffold, such as surface tension from a water drop, adhesives, and/or a biocompatible petroleum jelly.

Any of the fluid conduit 12, the outer sheath 14, and/or the support scaffold can contain or can be impregnated with a quantity of a drug. Alternatively, or in addition, a surface of these components can be coated with a drug. Exemplary drugs include anti-inflammatory components, drug permeability-increasing components, delayed-release coatings, and the like. In some embodiments, one or more components of the device 10 can be coated or impregnated with a corticosteroid such as dexamethasone which can prevent swelling around the injection site and disruptions to the fluid delivery pattern that can result from such swelling.

The device 10 can also include one or more sensors 22 mounted in or on the fluid conduit 12, the sheath 14, or the scaffold. The sensors 22 can include temperature sensors, pH sensors, pressure sensors, oxygen sensors, tension sensors, interrogatable sensors, glutamate sensors, ion concentration sensors, carbon dioxide sensors, lactate sensors, neurotransmitter sensors, or any of a variety of other sensor types, and can provide feedback to a control circuit which can in turn regulate the delivery of fluid through the device 10 based on one or more sensed parameters. One or more electrodes 24 can also be provided in or on the fluid conduit 12, the sheath 14, or the scaffold, which can be used to deliver electrical energy to target tissue, e.g., to stimulate the target tissue or to ablate the target tissue. In one embodiment, electrical energy is delivered through an electrode 24 while a drug is simultaneously delivered through the fluid conduit 12.

Figure 3:
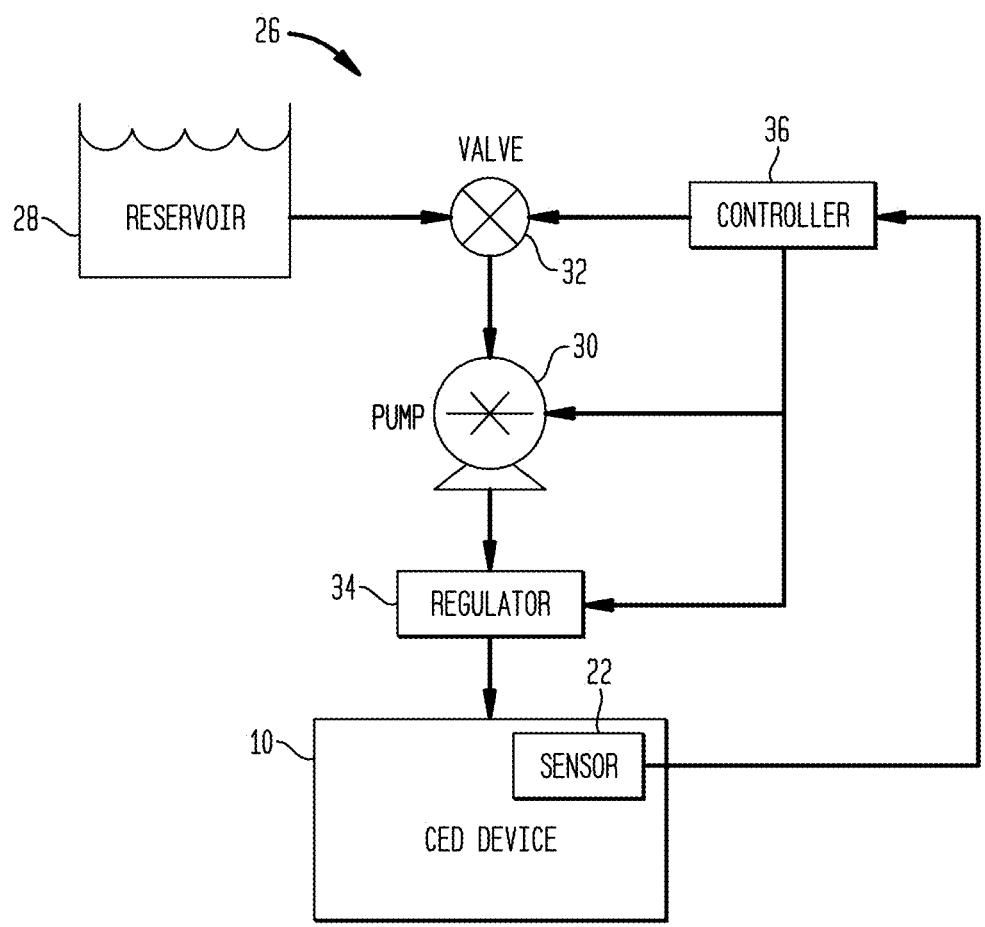
FIG. 3 is a schematic view of a fluid delivery system that includes the device of FIG. 1.

FIG. 3 is a schematic illustration of a drug delivery system 26 that includes the device 10. The system 26 includes a reservoir 28 of a drug-containing fluid that is coupled to a pump 30 via a control valve 32. When the control valve 32 is opened, fluid in the reservoir 28 is supplied under pressure by the pump 30 to a pressure regulator 34, which can adjust a pressure at which the fluid is supplied to the device 10. The control valve 32, pump 30, and regulator 34 can be operatively coupled to a controller 36 which can include a microprocessor and a memory and can be configured to execute a drug-delivery control program stored in a non-transitory computer-readable storage medium. The controller 36 can be configured to open or close the valve 32, to turn the pump 30 on or off, to change an output pressure of the pump 30, and/or to adjust a pressure set point of the regulator 34. The controller 36 can also receive information indicative of a sensed parameter via a feedback loop that includes one or more sensors 22 mounted in or on the device 10. Thus, in response to feedback from one or more sensors 22 implanted with the device 10, the controller 36 can start or stop the flow of fluid to the device 10, increase or decrease the pressure at which fluid is supplied to the device 10, etc. In one embodiment, the device 10 includes a pressure sensor 22 that measures a fluid pressure in the vicinity of the device 10 and the controller 36 is configured to maintain the fluid supply pressure at a substantially constant level based on feedback from the pressure sensor 22.

The device 10 can be used for CED of drugs to treat disorders of the brain, spine, ears, neural tissue, or other parts of a human or animal body. When used in the brain, the device 10 can circumvent the blood-brain barrier (BBB) by infusing drugs under positive pressure directly into tissue. The device 10 can provide a number of advantages, such as 1) a smaller cross-sectional area compared with conventional needles used in CED; 2) less disturbance to tissue when inserted into the brain than conventional needles; 3) the reduction or elimination of backflow or reflux along the outside of the inserted part, which in turn, permits higher rates of drug delivery in the device 10 compared with conventional needles; 4) minimal or no occlusion of the fluid delivery conduit 12 during insertion into the brain; 5) multiple lumens can be provided through the fluid conduit 12, each conducting a distinct fluid (drug), which allows simultaneous, sequential, or programmed delivery of multiple agents; 6) the device 10 has the potential to serve simultaneously as a drug delivery system and as a sensor-equipped probe to measure local tissue characteristics such as, but not limited to, pressure, pH, ion-specific concentrations, location, and other parameters; and 7) the device 10 allows for directional control of the drug release pattern.

In use, as described further below, the device 10 can be functionally attached to the distal end of a long, thin insertion vehicle such as a cannula or a needle in or on which a fluid attachment can be made to the fluid inlet port of the device's fluid conduit 12. This can be especially advantageous in applications involving penetration of relatively thick tissue, e.g., insertion through a human skull.

In addition to delivering a drug-containing fluid, the device 10 can also be used to deliver enzymes or other materials to modify tissue permeability and improve drug distribution in the targeted tissue. For example, penetration of drug-containing nanoparticles into brain tissue can be enhanced by enzymatic digestion of at least one brain extracellular matrix component and intracranial infusion of the nanoparticle into the brain tissue. In another embodiment, at least one enzyme can be immobilized to a surface of the nanoparticle during the step of enzymatic digestion. The device 10 can provide the ability to deliver enzymatic and/or other materials that can, e.g., modify the drug delivery site, and therapeutic materials, in virtually any order, sequencing, and/or timing without the need to use different delivery devices and the potential complications involved in doing so.

The device 10 can also be used to biopsy tissue, for example by passing a stylet or a grasping tool through the fluid conduit 12 to a target site and then withdrawing the stylet or grasping tool from the target site with a biopsy specimen therein. In some embodiments, the fluid conduit 12 can have a larger-diameter lumen extending therethrough for biopsy purposes, with smaller fluid lumens formed therearound.

Figure 4:
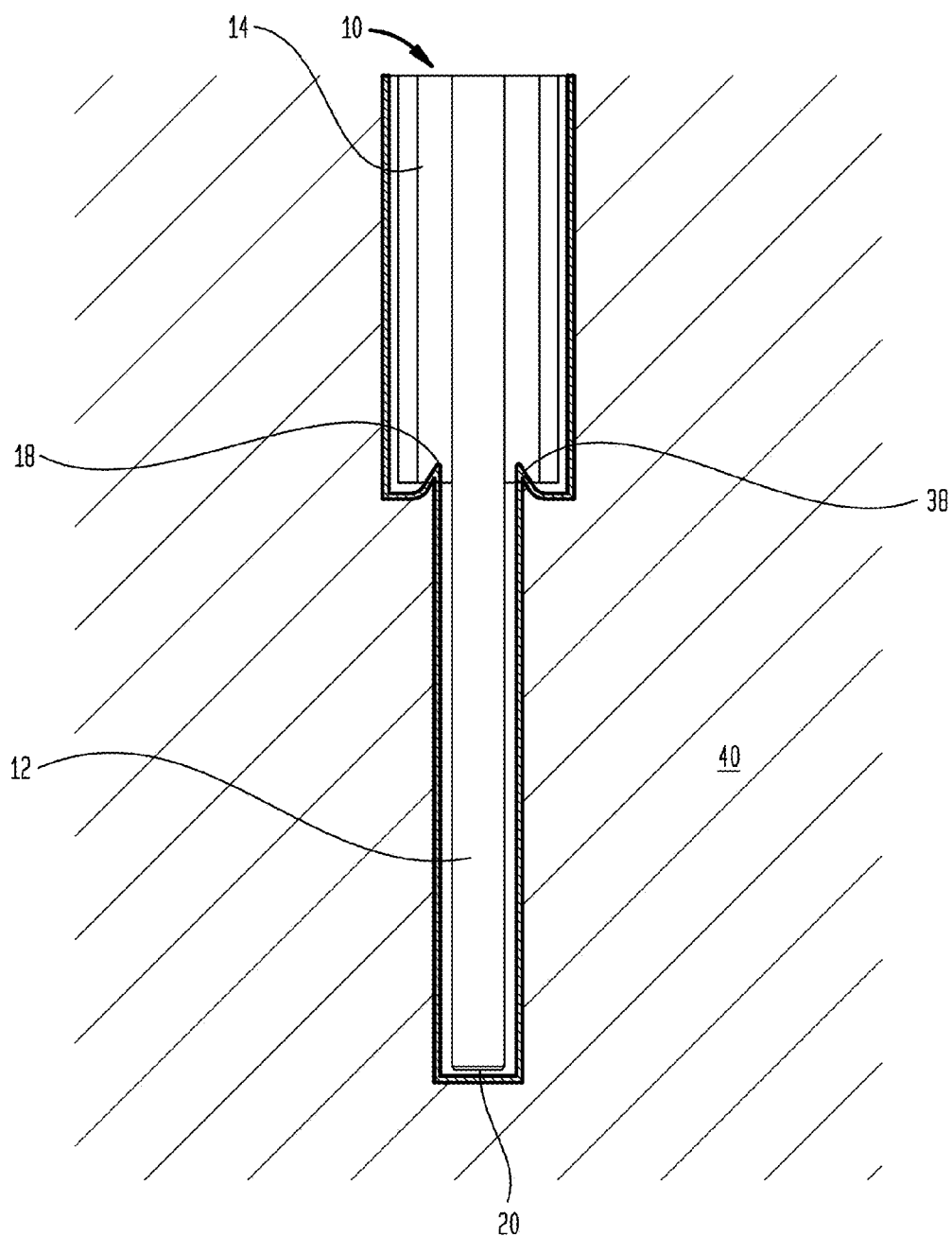
FIG. 4 is a schematic view of the device of FIG. 1 inserted into tissue.

The device 10 can be used to deliver a drug-containing fluid under positive pressure to a target tissue region. FIG. 4 illustrates an exemplary method for convection-enhanced delivery of a drug to target tissue 40 in a patient's brain. After appropriate site preparation and cleaning, a tissue opening can formed through the patient's scalp and skull to expose the brain tissue 40. Before or after forming the tissue opening, a pedestal can optionally be mounted to the patient to support the device 10 while it is inserted, which can be particularly useful in long-term implantations.

The device 10 can optionally be coupled to a cannula (not shown) with a microfabricated interface for mating with the device 10. Any of a variety of cannulas can be used, including standard cannulas configured to mate to a stereotactic frame in guided surgery. In some embodiments, the cannula can include a flexible catheter suitable for extended (e.g., 30 day) implantation. The catheter can be about 15 cm long and about 2 cm in diameter. The cannula can include a tubing portion that is approximately 6 feet in length with connectors for fluid and biosensor interface at the proximal end.

The device 10 can be advanced through the tissue opening and into the brain tissue 40. As shown, the tissue-receiving space 18 can be configured to compress or pinch tissue received therein as the device 10 is advanced through the tissue 40. Tissue compressed by the tissue-receiving space 18 can form a seal that reduces proximal backflow of fluid ejected from the outlet 20 of the fluid conduit 12 beyond the tissue-receiving space 18. In particular, as fluid ejected from the outlet 20 of the fluid conduit 12 flows back proximally between the exterior surface of the fluid conduit 12 and the surrounding tissue 40, it encounters a shoulder of tissue 38 that is compressed into the tissue-receiving space 18. Compression of the tissue 38 against the walls of the tissue-receiving space 18 forms a seal that resists flow of the fluid further in the proximal direction, thereby reducing or preventing undesirable backflow of injected fluid away from the target region of the tissue.

As explained above, the device 10 can include a support scaffold to facilitate penetration through the brain tissue towards the target region. One or more radiopaque markers can be included in the device 10 to permit radiographic imaging (e.g., to confirm proper placement of the device 10 within or in proximity to the target tissue). In embodiments in which a degradable scaffold is used, the scaffold can degrade shortly after insertion to leave behind only the fluid conduit 12 and outer sheath 14. In some embodiments, the fluid conduit 12 and/or the sheath 14 can be flexible to permit the device 10 to move with the brain tissue 40 if the brain tissue 40 shifts within the skull. This can advantageously prevent localized deformation of brain tissue adjacent to the device 10 that might otherwise occur with a rigid device. Such deformation can lead to backflow of the pressurized fluid along the surface of the device, undesirably preventing the fluid from reaching the target tissue.

Once the device 10 is positioned within or adjacent to the target tissue, injected media (e.g., a drug-containing fluid) can be supplied under positive pressure to the device 10 through its fluid inlet port(s). The injected media then flows through the fluid conduit 12 and is expelled under pressure from the outlet port(s) 20 in the target region of tissue. The delivery profile can be adjusted by varying parameters such as outlet port size, outlet port shape, fluid conduit size, fluid conduit shape, fluid supply pressure, fluid velocity, etc. In some embodiments, the device 10 can be configured to deliver fluid at a flow rate between about 5 µl per minute and about 20 µl per minute. In some embodiments, the device 10 can be configured to deliver 50-100 µl per minute per channel, and each channel can be configured to support greater than 100 psi of pressure.

In some embodiments, prior to injecting the drug-containing fluid, a gel or other material can be injected through the device 10 to augment the tissue seal. For example, a sealing gel can be injected through the device 10 and allowed to flow back along the exterior of the device, filling and sealing any voids that may exist between the device and the surrounding tissue, particularly within the tissue-receiving recess 18. Exemplary sealing materials include cyanoacrylate, protein glues, tissue sealants, coagulative glues (e.g., fibrin/thrombin/protein based coagulative glues), and materials such as those disclosed in U.S. Publication No. 2005/0277862, filed on Jun. 9, 2004, entitled "SPLITABLE TIP CATHETER WITH BIORESORBABLE ADHESIVE," the entire contents of which are incorporated herein by reference.

It will be appreciated from the foregoing that the methods and devices disclosed herein can provide convection-enhanced delivery of functional agents directly to target tissue within a patient with little or no backflow. This convection-enhanced delivery can be used to treat a broad spectrum of diseases, conditions, traumas, ailments, etc. The term "drug" as used herein refers to any functional agent that can be delivered to a human or animal patient, including hormones, stem cells, gene therapies, chemicals, compounds, small and large molecules, dyes, antibodies, viruses, therapeutic agents, etc.

In some embodiments, central-nervous-system (CNS) neoplasm can be treated by delivering an antibody (e.g., an anti-epidermal growth factor (EGF) receptor monoclonal antibody) or a nucleic acid construct (e.g., ribonucleic acid interference (RNAi) agents, antisense oligonucleotide, or an adenovirus, adeno-associated viral vector, or other viral vectors) to affected tissue. Epilepsy can be treated by delivering an anti-convulsive agent to a target region within the brain. Parkinson's disease can be treated by delivering a protein such as glial cell-derived neurotrophic factor (GDNF) to the brain. Huntington's disease can be treated by delivering a nucleic acid construct such as a ribonucleic acid interference (RNAi) agent or an antisense oligonucleotide to the brain. Neurotrophin can be delivered to the brain under positive pressure to treat stroke. A protein such as a lysosomal enzyme can be delivered to the brain to treat lysosomal storage disease. Alzheimer's disease can be treated by delivering anti-amyloids and/or nerve growth factor (NGF) under positive pressure to the brain. Amyotrophic lateral sclerosis can be treated by delivering a protein such as brain-derived neurotrophic factor (BDNF) or ciliary neurotrophic factor (CNTF) under positive pressure to the brain, spinal canal, or elsewhere in the central nervous system. Chronic brain injury can be treated by delivering a protein such as brain-derived neurotrophic factor (BDNF) and/or fibroblast growth factor (FGF) under positive pressure to the brain.

It will be appreciated that use of the devices disclosed herein and the various associated treatment methods is not limited to the brain of a patient. Rather, these methods and devices can be used to deliver a drug to any portion of a patient's body, including the spine. By way of further example, balance or hearing disorders can be treated by injecting a drug-containing fluid directly into a portion of a patient's ear. Any of a variety of drugs can be used to treat the ear, including human atonal gene. The methods and devices disclosed herein can also be used to deliver therapeutics (such as stem cells) to a fetus or to a patient in which the fetus is disposed. The methods and devices disclosed herein can be used to treat a cavernous malformation, for example by delivering one or more antiangiogenesis factors thereto.

Any of the various treatments described herein can further include delivering a cofactor to the target tissue, such as a corticosteroid impregnated in the device, a corticosteroid coated onto the device, and/or a propagation enhancing enzyme. In addition, any of the various treatments described herein can further include long-term implantation of the device (e.g., for several hours or days) to facilitate long-term treatments and therapies.

A number of variations on the device 10 are set forth below. Except as indicated, the structure and operation of these variations is identical to that of the device 10, and thus a detailed description is omitted here for the sake of brevity.

Figure 5:
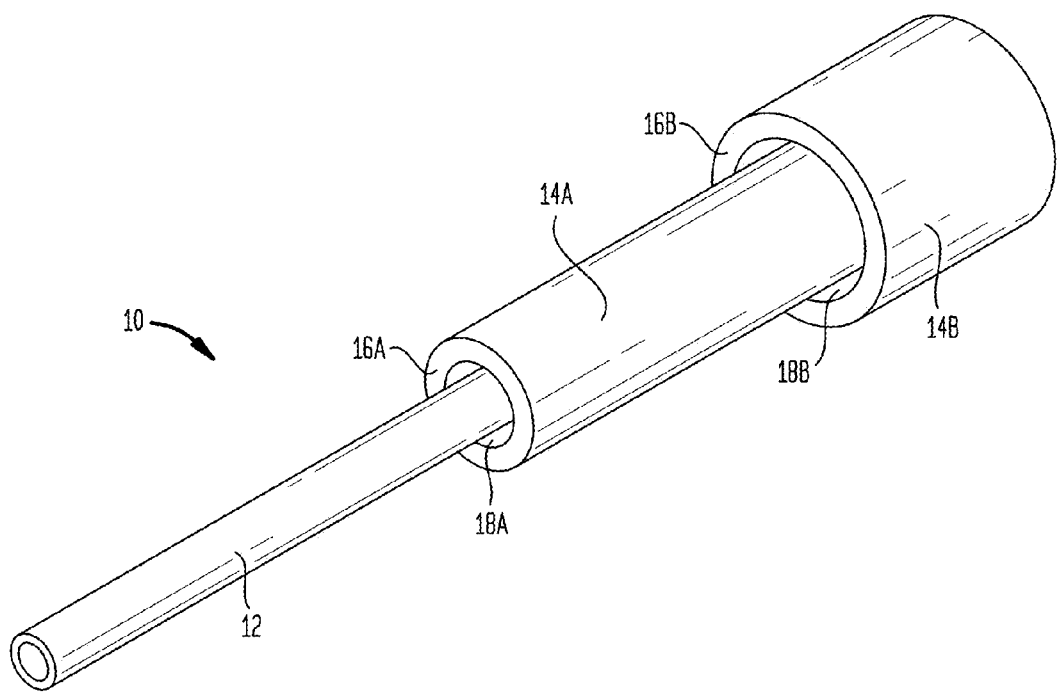
FIG. 5 is a perspective view of another exemplary embodiment of a CED device.

In some embodiments, the device 10 can include a plurality of tissue-receiving spaces 18. FIG. 5 illustrates an embodiment with a first tissue-receiving space 18A and a second tissue-receiving space 18B. As shown, a first outer sheath 14A is disposed over the fluid conduit 12 to define the first tissue-receiving space 18A. A second outer sheath 14B is disposed over the first outer sheath 14A to define the second tissue-receiving space 18B. Specifically, the second tissue-receiving space 18B is formed between an exterior surface of the first outer sheath 14A and an interior surface of the distal end 16B of the second outer sheath 14B. While two tissue-receiving spaces are shown, it will be appreciated that any number of tissue-receiving spaces can be provided (e.g., three, four, five, or more) by adding additional sheath layers. A single sheath layer can also be configured to provide multiple tissue-receiving spaces, for example by forming the sheath layer with one or more stepped regions, each stepped region defining a tissue-receiving space therein. Multi-stage devices such as that shown in FIG. 5 can provide additional sealing regions proximal to the distal-most, primary sealing region. The provision of these secondary, tertiary, etc. sealing regions can augment the primary seal or act as a backup in case the primary seal is compromised.

Figure 6A:
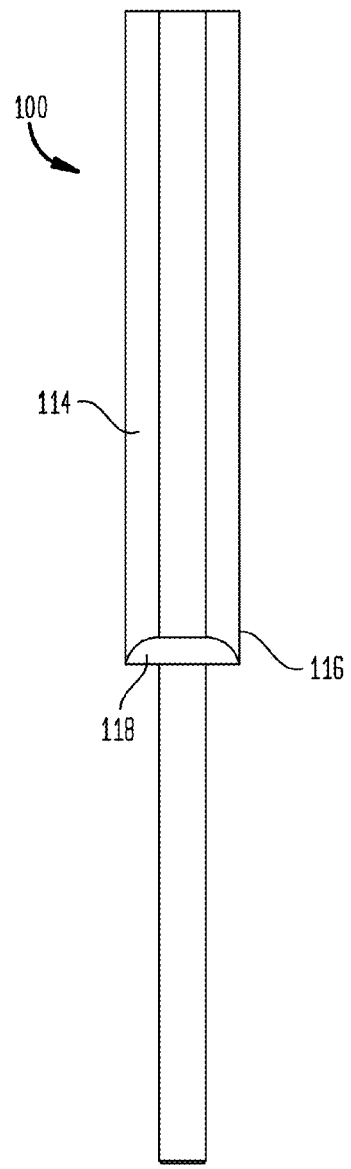
FIG. 6A is a plan view of another exemplary embodiment of a CED device.
Figure 6B:
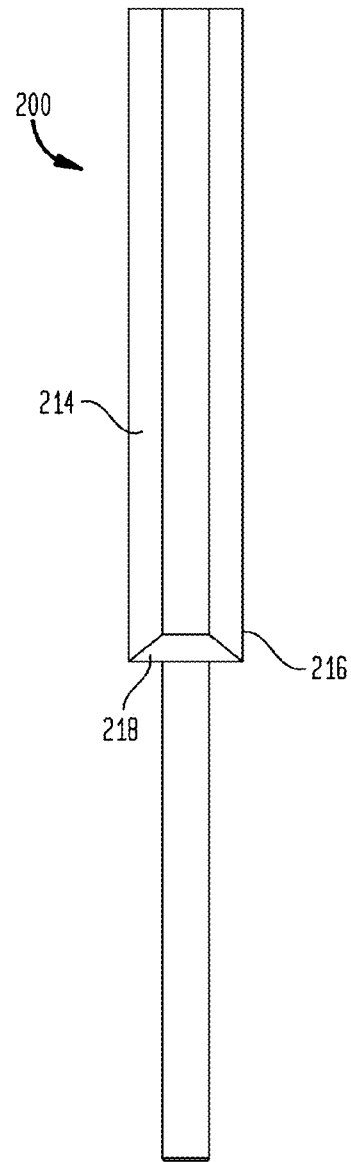
FIG. 6B is a plan view of another exemplary embodiment of a CED device.
Figure 6C:
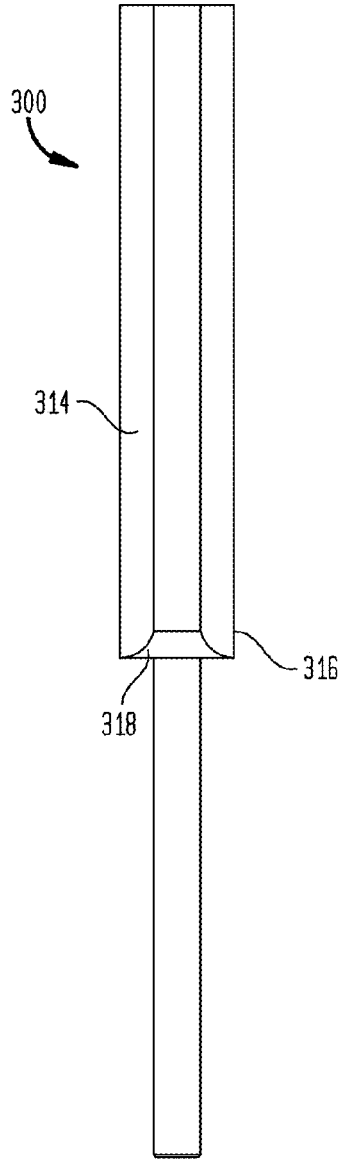
FIG. 6C is a plan view of another exemplary embodiment of a CED device.

As shown in FIGS. 6A-6C, the internal wall of the distal end 16 of the outer sheath 14 can be shaped to alter the dimensions of the tissue-receiving space 18 and the type of seal provided when tissue is compressed therein. FIG. 6A illustrates a device 100 in which the interior surface of the distal end 116 of the sheath 114 has a concave curvature. FIG. 6B illustrates a device 200 in which the interior surface of the distal end 216 of the sheath 214 is conical. FIG. 6C illustrates a device 300 in which the interior surface of the distal end 316 of the sheath 314 has a convex curvature. These configurations can provide for a sharper leading edge at the periphery of the sheath as compared with the cylindrical tissue-receiving space 18 of the device 10, and can increase the amount of tissue compressed into or pinched/pinned by the tissue-receiving space, as well as the degree of compression. A more-robust seal can thus be obtained in some instances using the configurations of FIGS. 6A-6C. It should be noted, however, that even in the case of a cylindrical tissue-receiving space, the leading edge of the sheath can be sharpened to deflect tissue into the tissue-receiving space and thereby form a better seal. The size and shape of the tissue-receiving space can be selected based on a variety of parameters, including the type of tissue in which the device is to be inserted. In embodiments with a plurality of tissue-receiving spaces, each of the tissue receiving spaces can have the same configuration (e.g., all cylindrical, all conical, all convex, or all concave). Alternatively, one or more of the plurality of tissue-receiving spaces can have a different configuration. Thus, for example, one or more tissue-receiving spaces can be cylindrical while one or more other tissue receiving spaces are convex.

The tissue-receiving recesses of the devices disclosed herein can include various surface features or treatments to enhance the seal formed between the device and the surrounding tissue or gel. For example, the tissue-receiving recesses can be coated with a biocompatible adhesive or can have a textured surface to form a tighter seal with the tissue or gel.

FIG. 7 illustrates an exemplary embodiment of a CED device 400 that generally includes a fluid conduit in the form of a micro-tip 412 and an outer sheath 414. The micro-tip 412 includes a substrate 442, which can be formed from a variety of materials, including silicon. The substrate 442 can have any of a variety of cross-sectional shapes, including a square or rectangular cross-section as shown. One or more fluid channels 444 can be formed on the substrate 442. The fluid channels 444 can be formed from a variety of materials, including parylene. Additional details on the structure, operation, and manufacture of microfabricated tips such as that shown in FIG. 7 can be found in U.S. Publication No. 2013/0035560, filed on Aug. 1, 2012, entitled "MULTI-DIRECTIONAL MICROFLUIDIC DRUG DELIVERY DEVICE," the entire contents of which are incorporated herein by reference.

The outer sheath 414 can be disposed coaxially over the micro-tip 412 so as to form a tissue-receiving space 418 therebetween. In some embodiments, the micro-tip 412 can have a substantially rectangular exterior cross-section and the outer sheath 414 can have a substantially cylindrical interior cross-section. In other embodiments, the micro-tip 412 and the outer sheath 414 can have corresponding cross-sectional shapes with a clearance space defined therebetween. The proximal end of the outer sheath 414 can be coupled to a catheter 446. The catheter 446 can be rigid or flexible, or can include rigid portions and flexible portions. A nose portion 448 (sometimes referred to herein as a "bullet nose" or a "bullet nose portion") can be disposed between the outer sheath 414 and the catheter 446, or can be disposed over a junction between the outer sheath 414 and the catheter 446. As shown, the nose portion 448 can taper from a reduced distal diameter corresponding to the outside diameter of the sheath 414 to an enlarged proximal diameter corresponding to the outside diameter of the catheter 446. The tapered transition provided by the nose portion 448 can advantageously provide stress-relief as it can act as a smooth transition from the sheath 414 to the catheter body 446, avoiding any uneven stresses on the surrounding tissue that may create paths for fluid backflow. The nose portion 448 can be conically tapered, as shown, or can taper along a convex or concave curve. Various compound shapes can also be used that include conical portions, convex portions, and/or concave portions. The nose portion 448 can also be replaced with a blunt shoulder that extends perpendicular to the longitudinal axis of the device 400. Any of a variety of taper angles can be used for the nose portion 448. For example the nose portion 448 can taper at an angle in a range of about 10 degrees to about 90 degrees relative to the longitudinal axis of the device 400, in a range of about 20 degrees to about 70 degrees relative to the longitudinal axis of the device, and/or in a range of about 30 degrees to about 50 degrees relative to the longitudinal axis of the device. For example, the nose portion 446 can taper at an angle of approximately 33 degrees relative to the longitudinal axis of the device 400. In some embodiments, additional sheaths can be provided, e.g., as described above with respect to FIG. 5.

As shown in FIG. 8, the catheter 446 can include length markings or graduations 450 to indicate the insertion depth of the device 400. In some embodiments, the catheter 446 can be a straight rigid catheter sized and configured for acute stereotactic targeting. The catheter 446 can be formed from any of a variety of materials, including flexible materials, rigid materials, ceramics, plastics, polymeric materials, PEEK, polyurethane, etc. and combinations thereof. In an exemplary embodiment, the catheter 446 has length of about 10 cm to about 40 cm, e.g., about 25 cm. The catheter 446 can include one or more fluid lines extending therethrough. The fluid lines can be defined by the catheter body itself or can be defined by one or more inner sleeves or linings disposed within the catheter body. Any of a variety of materials can be used to form the inner sleeves or linings, such as flexible materials, rigid materials, polyimide, pebax, PEEK, polyurethane, silicone, fused silica tubing, etc. and combinations thereof.

Figure 9:
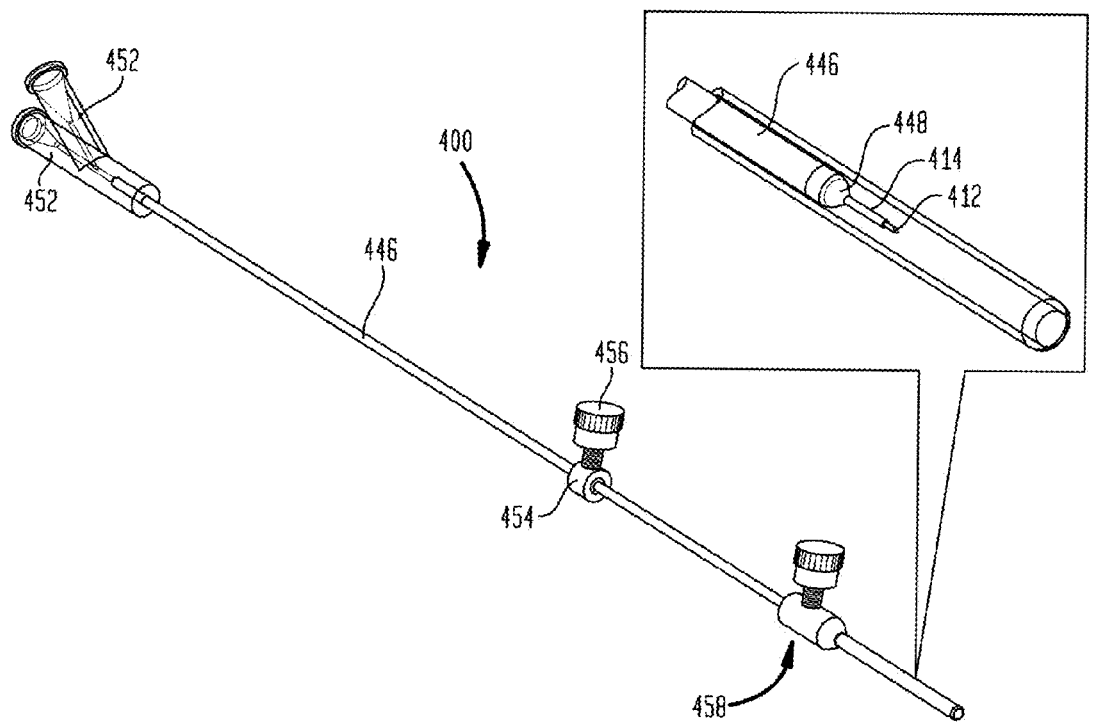
FIG. 9 is a perspective view of the CED device of FIG. 7 with a depth stop and tip protector.

As shown in FIG. 9, one or more standard Luer or other connectors 452 can be coupled to the proximal end of the catheter 446 to facilitate connection with a fluid delivery system of the type shown in FIG. 3. In the illustrated embodiment, the system 400 includes two connectors 452, one for each of the two fluid channels formed in the catheter 446 and the micro-tip 412. It will be appreciated, however, that any number of fluid channels and corresponding proximal catheter connectors can be provided. The system 400 can also include a collar 454 disposed over the catheter 446 to act as a depth stop for setting the desired insertion depth and preventing over-insertion. The collar 454 can be longitudinally slidable with respect to the catheter 446 and can include a thumb screw 456 for engaging the catheter to secure the collar in a fixed longitudinal position with respect thereto. The system 400 can also include a tip protector 458 for preventing damage to the micro-tip 412 during insertion into stereotactic frame fixtures. Exemplary tip protectors are disclosed in U.S. Provisional Application No. 61/835,905, filed on Jun. 17, 2013, entitled "METHODS AND DEVICES FOR PROTECTING CATHETER TIPS," the entire contents of which are incorporated herein by reference.

Figure 10:
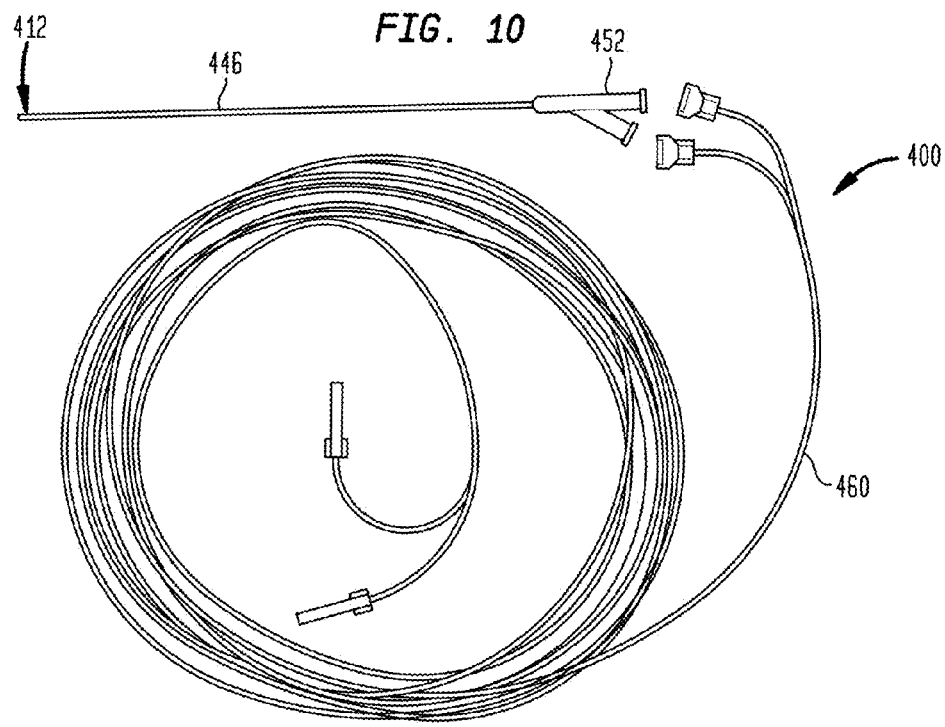
FIG. 10 is a plan view of the CED device of FIG. 7 with a length of extension tubing.

As shown in FIG. 10, the system 400 can include a length of extension tubing 460 to provide a fluid pathway between the proximal connectors 452 of the catheter 446 and a fluid delivery system of the type shown in FIG. 3. In the illustrated embodiment, dual-channel peel-away extension lines 460 are shown. In an exemplary method of using the system 400, an incision can be formed in a patient and the catheter 446 can be inserted through the incision and implanted in a target region of tissue (e.g., a region of the patient's brain or central nervous system). The catheter 446 can be left in the target region for minutes, hours, days, weeks, months, etc. In the case of a flexible catheter 446, the proximal end of the catheter can be tunneled under the patient's scalp with the proximal connectors 452 extending out from the incision. The catheter 446 can be inserted through a sheath to keep the catheter stiff and straight for stereotactic targeting. Alternatively, or in addition, a stylet can be inserted through the catheter to keep the catheter stiff and straight for stereotactic targeting. In some embodiments, the stylet can be inserted through an auxiliary lumen formed in the catheter such that the primary fluid delivery lumen(s) can be primed with fluid during catheter insertion. Thus, in the case of a catheter with first and second fluid lumens, a third lumen can be included for receiving the stylet.

Figure 11:
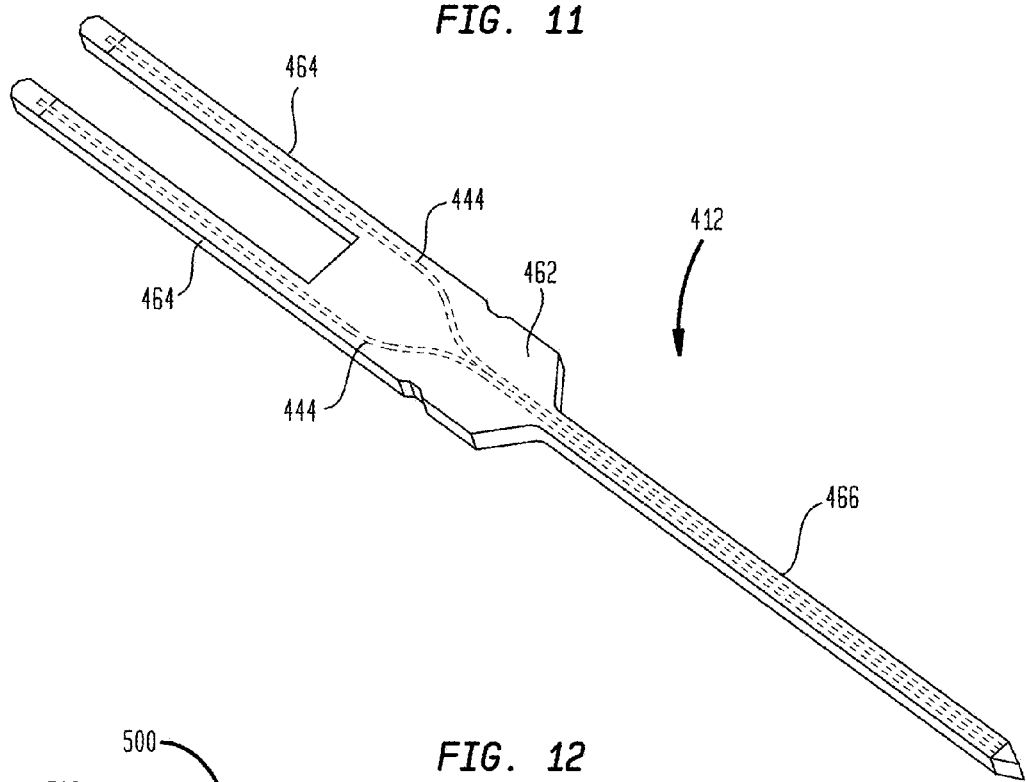
FIG. 11 is a perspective view of a micro-tip of the CED device of FIG. 7.

FIG. 11 is a close-up view of the exemplary micro-tip 412. As shown, the micro-tip 412 generally includes a central body portion 462 with first and second legs or tails 464 extending proximally therefrom and a tip portion 466 extending distally therefrom. First and second microfluidic channels 444 are formed in or on the micro-tip 412 such that they extend along the proximal legs 464, across the central body portion 462, and down the distal tip portion 466. The channels 444 can each include one or more fluid inlet ports (e.g., at the proximal end) and one or more fluid outlet ports (e.g., at the distal end). As noted above, additional details on the structure, operation, and manufacture of microfabricated tips such as that shown in FIG. 11 can be found in U.S. Publication No. 2013/0035560, filed on Aug. 1, 2012, entitled "MULTI-DIRECTIONAL MICROFLUIDIC DRUG DELIVERY DEVICE," the entire contents of which are incorporated herein by reference.

Systems and methods for manufacturing and/or assembling the CED device 400 are shown in FIGS. 12-15. Generally speaking, after the micro-tip 412 is fabricated, it can be positioned in a molding or casting system to couple the one or more sheaths 414 to the micro-tip, to form the nose portion 448, and/or to couple fluid lines in the catheter 446 to the fluid channels 444 of the micro-tip.

Figure 12:
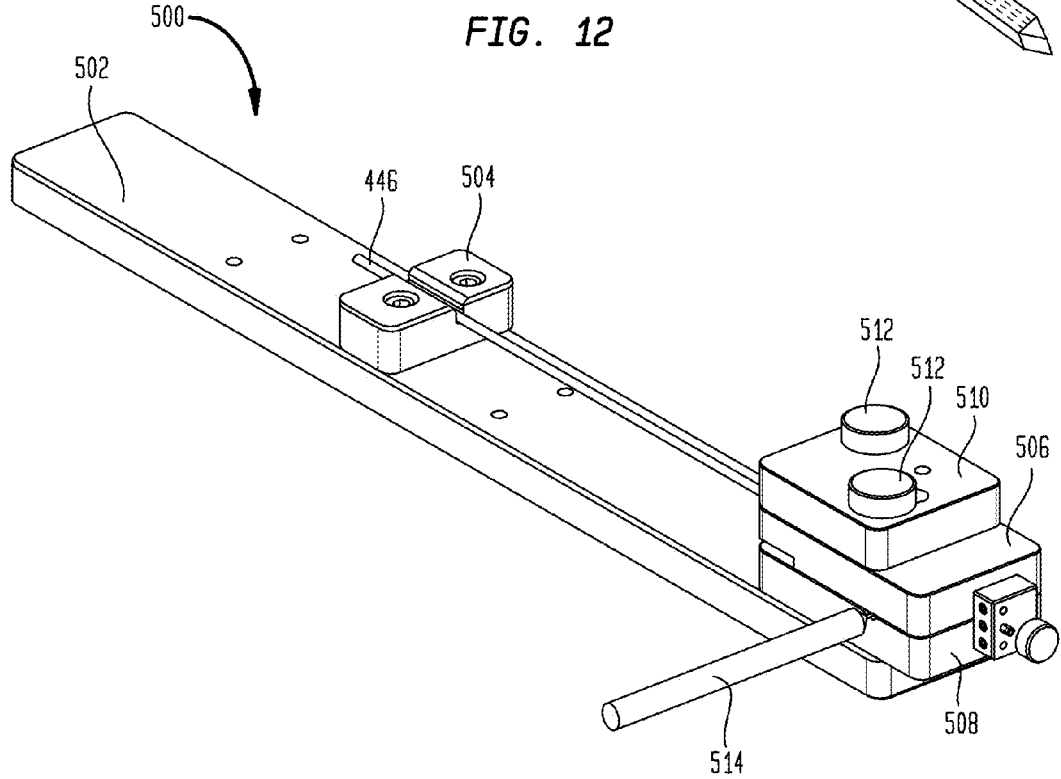
FIG. 12 is a perspective view of an exemplary embodiment of a molding system.

FIG. 12 illustrates an exemplary embodiment of a molding system 500. The system 500 includes a base plate 502 with a cradle 504 in which a proximal portion of the catheter 446 is supported. Upper and lower mold blocks 506, 508 are coupled to the base plate 502 by a clamping block 510 with one or more screws 512. The screws 512 can be tightened to lock the mold blocks 506, 508 in position during an injection process and can be removed to allow the mold blocks to be opened for insertion or removal of the CED device components. The system 500 also includes an inlet port 514 through which flowable material can be injected, pumped, etc. into the mold.

Figure 13:
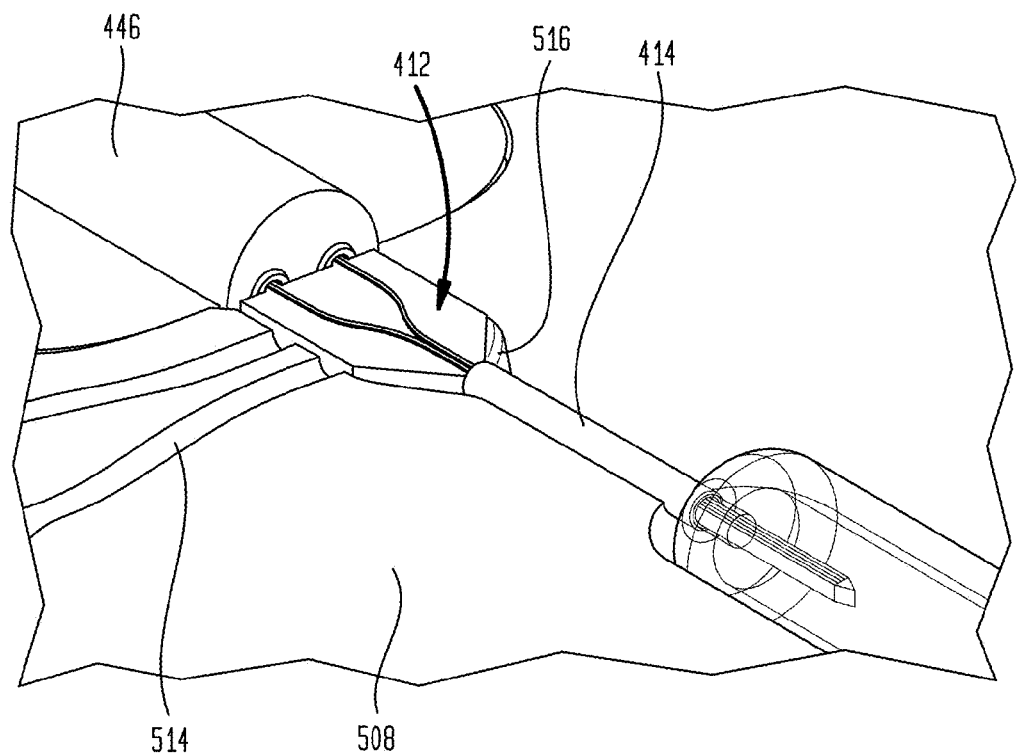
FIG. 13 is a perspective view of the CED device of FIG. 7 being manufactured using the molding system of FIG. 12.
Figure 14:
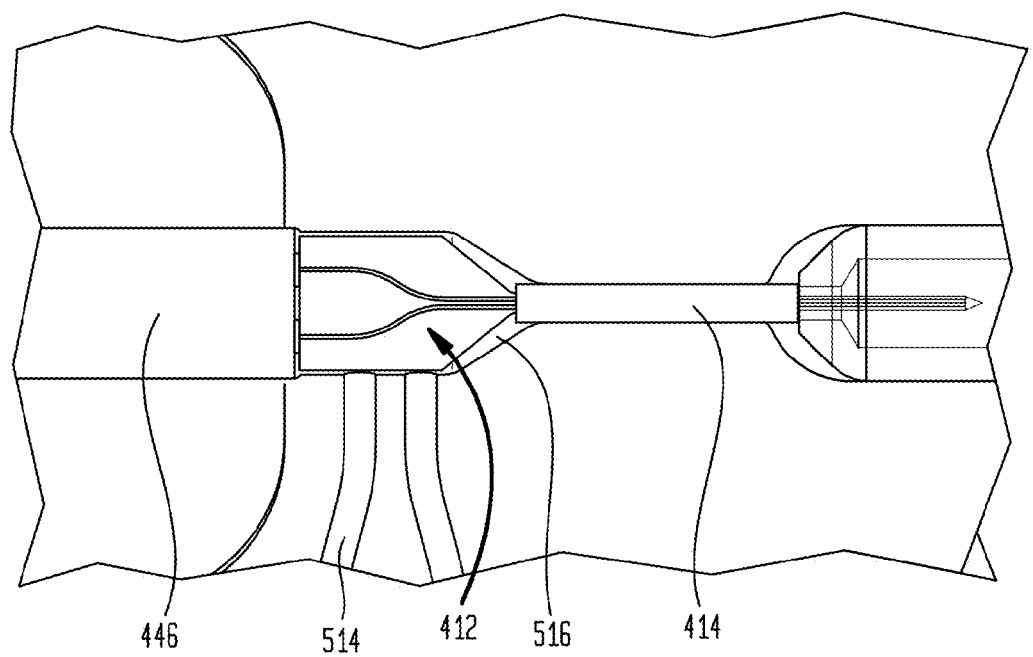
FIG. 14 is a top view of the CED device of FIG. 7 being manufactured using the molding system of FIG. 12.
Figure 15:
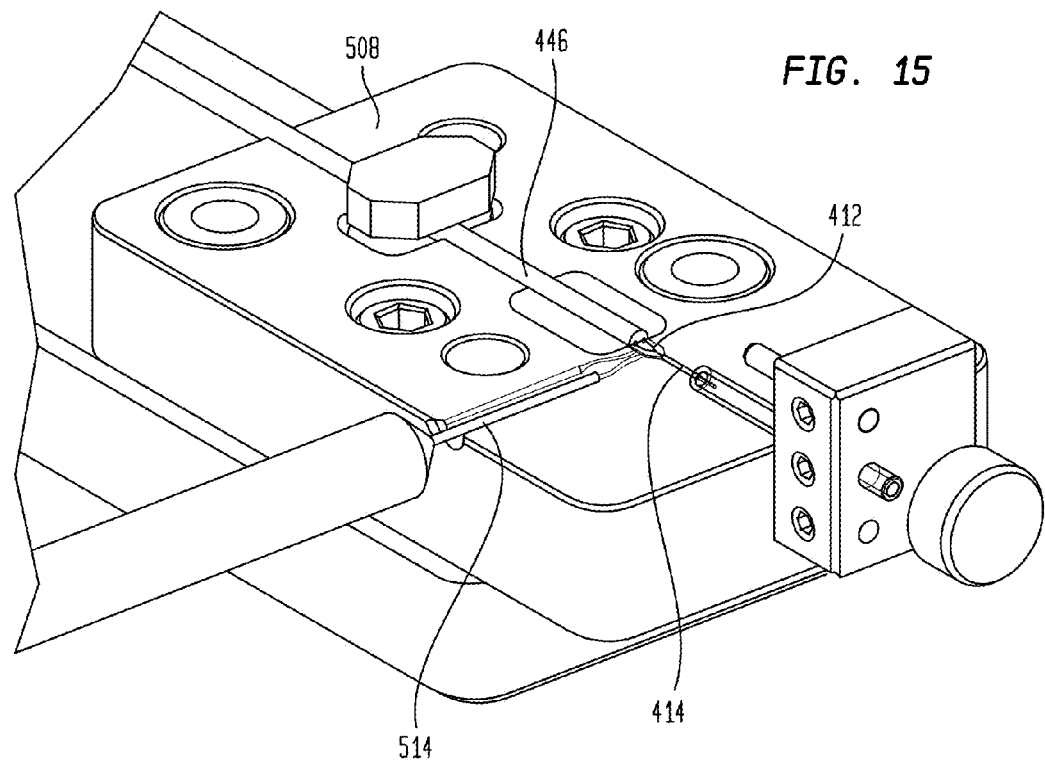
FIG. 15 is another perspective view of the CED device of FIG. 7 being manufactured using the molding system of FIG. 12.
Figure 16:
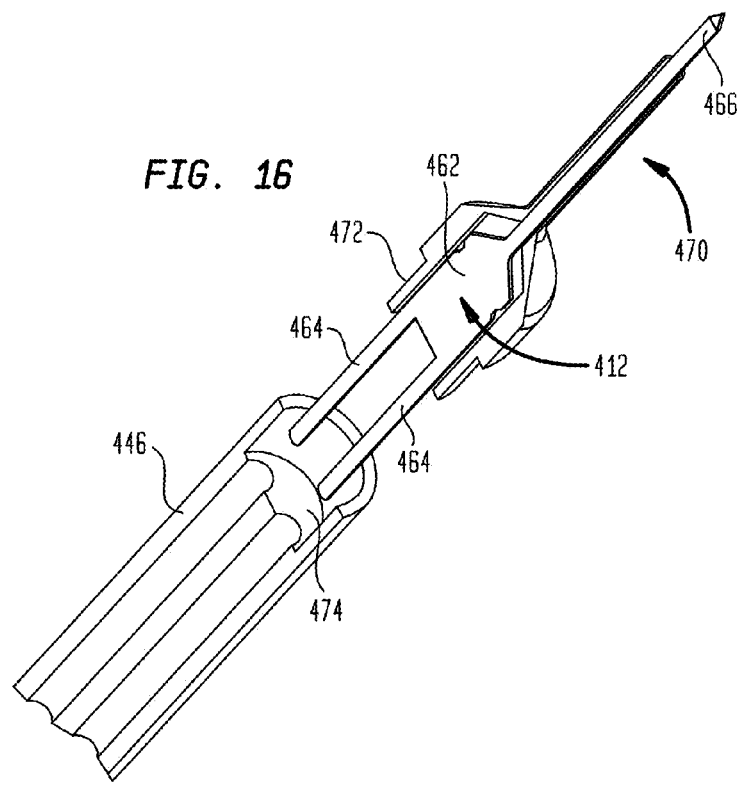
FIG. 16 is a partially-exploded sectional perspective view of another exemplary embodiment of a CED device.
Figure 17:
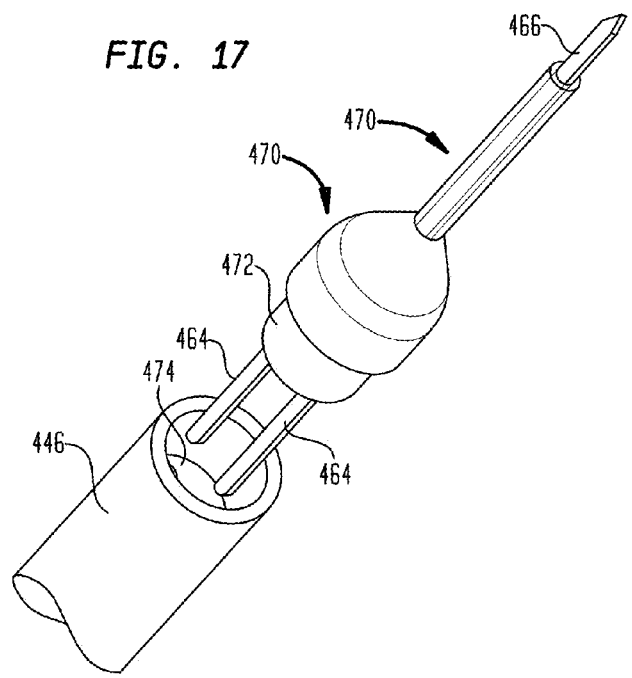
FIG. 17 is a partially-exploded perspective view of the CED device of FIG. 16.
Figure 18:
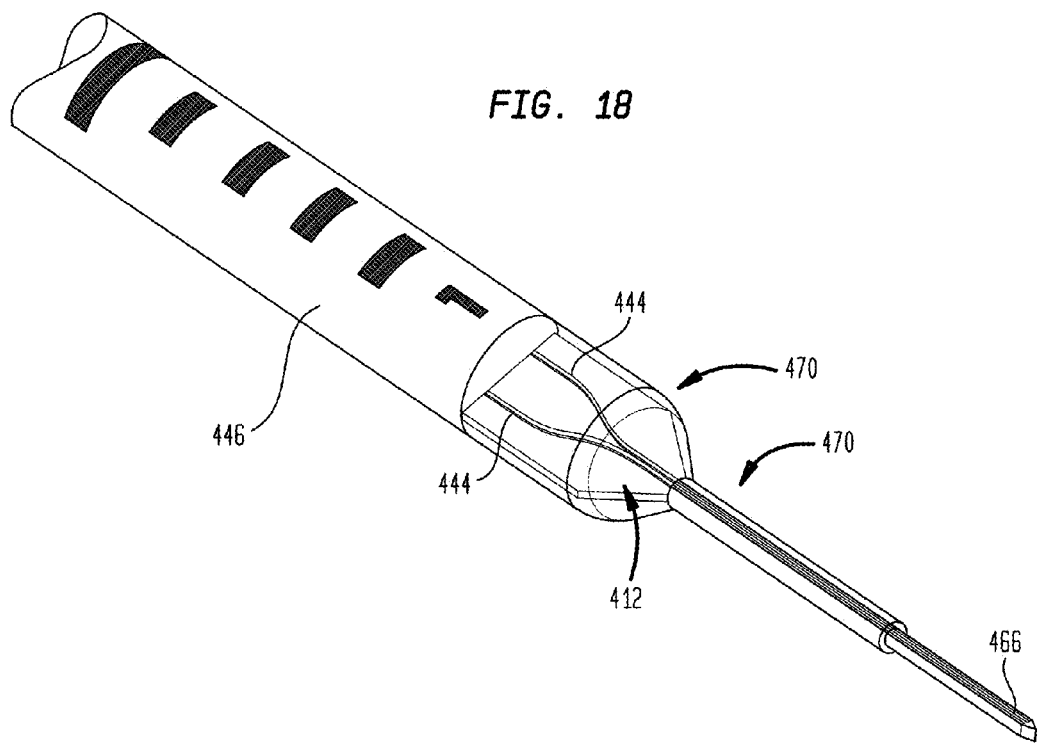
FIG. 18 is a perspective view of the CED device of FIG. 16.
Figure 19:
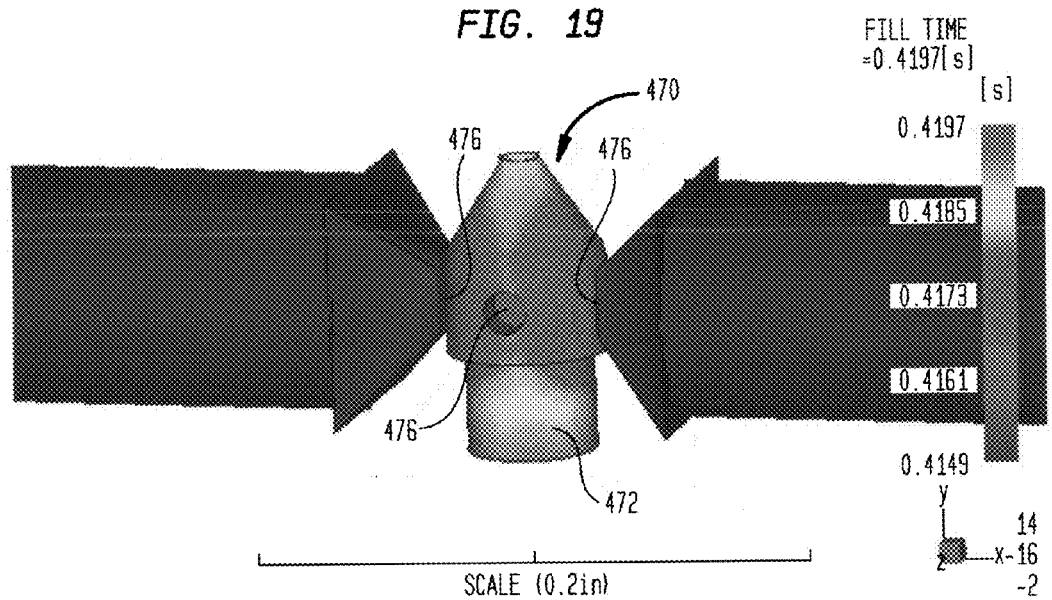
FIG. 19 is a map of mold filling time for the nose portion of the CED device of FIG. 16.

As shown in FIGS. 13-15, the lower mold block 508 includes a recess in which the lower half of the catheter body 446 can be disposed and a recess in which the lower half of the sheath 414 can be disposed. A mold cavity 516 which is substantially a negative of the lower half of the nose portion 448 is formed between the recesses. The recesses can be sized such that the catheter body 446 and the sheath 414 form a seal with the mold block 508 to prevent flowable material injected into the mold cavity 516 from escaping. One or more injection ports or channels 514 are formed in the mold block 508 to allow flowable material to be injected into the cavity 516. While not shown, it will be appreciated that the upper mold block 506 is configured in a similar manner to the lower mold block 508, with recesses that can receive the upper halves of the catheter body 446 and the sheath 414 and a mold cavity 516 which is substantially a negative of the upper half of the nose portion 448.

In use, the micro-tip 412 is positioned such that the proximal legs 464 are disposed within respective fluid lines formed in the catheter body 446 and such that the distal tip portion 466 of the micro-tip is positioned within the inner lumen of the sheath 414. As noted above, in some embodiments, the catheter fluid lines can be formed by inner linings (e.g., fused silica tubes) encased in an outer housing (e.g., a ceramic housing) that defines the catheter body 446. The inner linings can prevent leaks and hold the catheter body 446 together in the event that the outer housing is cracked or damaged. The micro-tip 412, catheter body 446, and sheath 414 are sandwiched between the upper and lower mold blocks 506, 508 and a flowable material is injected through the mold channels 514 to form the nose portion 448 within the mold cavity 516, and to couple the fluid lines in the catheter 446 to the fluid channels 444 of the micro-tip. Exemplary flowable materials include UV resins, polymers such as polyurethanes, acrylics, PTFE, ePTFE, polyesters, and so forth.

The flowable material can be injected at low rates to fill the cavity 516. In embodiments in which UV resin is used, the upper and lower mold blocks 506, 508 can be made of a clear material to allow UV light to cure the UV resin. As the UV resin is injected into the micro-mold cavity 516, it can start to wick/flow up over the micro-tip tails 464 and under the fluid lines that sit over the tails. Once the resin flows into the fluid lines, it can be flashed with UV light to "freeze" it in place and avoid wicking/flowing too much (and not completely encapsulating the tails 464 and the inlet holes on the tips of the tails). After the material cures, the mold blocks 506, 508 can be separated and the CED device 400 can be removed from the molding system 500.

It will be appreciated that the above systems and methods can be varied in a number of ways without departing from the scope of the present disclosure. For example, the molding process can be used only for coupling the fluid lines, and the bullet nose portion can be formed using a different process once the fluid connections are made. Also, while wicking is described herein as the mechanism by which the fluid line bonds are formed, it will be appreciated that these bonds can also be controlled by fill pressure, timing, and other molding variables. The bullet nose can be over-molded directly onto the micro-tip. While an exemplary micro-tip and an exemplary catheter body are shown, it will be appreciated that the micro-molding methods and devices disclosed herein can be used with any of a variety of tips and/or catheters.

Alternative systems and methods for manufacturing and/or assembling the CED device 400 are shown in FIGS. 16-21. As shown in FIGS. 16-19, the bullet nose and the one or more sheaths or over tubes can be assembled separately using an over-molding process as described below to create a molded part 470. To assemble the system 400, the proximal legs 464 of the micro-tip 412 are inserted into the distal end of the catheter body 446 (e.g., by inserting each leg into a respective lining disposed within an outer catheter housing). A flowable material (e.g., an adhesive such as a UV curable adhesive) can then be applied to the legs 464 to bond the fluid channels on each leg to a corresponding fluid line of the catheter body 446. The molded part 470 can then be slid over the distal end of the micro-tip 412 such that the central body portion 462 of the micro-tip is disposed in a hollow interior of the molded part and such that the tip portion 466 of the micro-tip extends through the molded part and protrudes from the distal end thereof.

The molded part 470 can include a shoulder that defines a proximal male portion 472 that mates into a female counterbore 474 formed in the distal tip of the catheter body 446. Alternatively, the catheter body 446 can define a male portion and the molded part 470 can include a female counterbore. It will also be appreciated that other ways of mating the catheter body 446 to the molded part 470 can be used, such as a threaded interface, a snap-fit interface, a key and slot interface, or any other interlocking interface that provides alignment and/or overlap between the molded part and the catheter body. In some embodiments, the counterbore 474 can be formed by machining a recess into the distal end of a ceramic catheter body 446. The inner linings of the catheter can then be inserted into the ceramic outer housing such that the terminal ends of the inner linings are flush with the floor of the counterbore 474. The molded part 470 can be attached to the catheter body 446 using a flowable material (e.g., a UV adhesive), which can be applied to the counterbore 474 and/or the male portion 472 prior to assembling the components or which can be applied through one or more openings 476 formed in the sidewall of the molded part after the components are assembled or dry fit. The flowable material is allowed to cure to form a seal between the fluid lines and to secure the components of the CED device 400 to one another.

Figure 20:
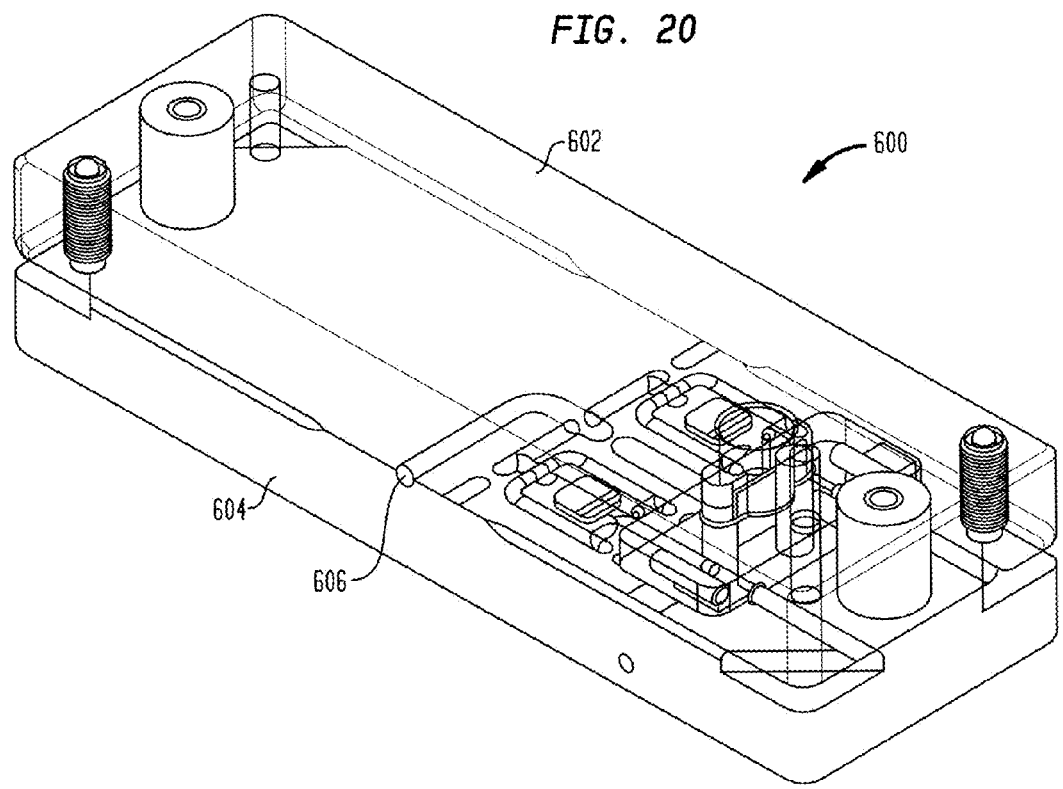
FIG. 20 is a perspective view of an exemplary embodiment of a molding system for forming the nose portion of the CED device of FIG. 16.

An exemplary over-molding system 600 for forming the bullet nose and coupling the bullet nose to one or more over-tubes to form the molded part 470 is shown in FIG. 20. The molding system 600 includes upper and lower plates 602, 604 that sandwich the one or more over-tubes and together define a negative of the bullet nose. The plates 602, 604 also define a plug for forming the bullet nose as a hollow structure which can later be filled as described above during final assembly. A flowable material can be injected through injection ports 606 formed in the plates 602, 604 using a syringe or pump to form the hollow bullet nose over the one or more over-tubes. In some embodiments, the flowable material is a hot resin injected under pressure which forms a strong hold with the over-tube upon curing. The over-tube can be formed from any of a variety of materials, including fused silica tubing.

Figure 21:
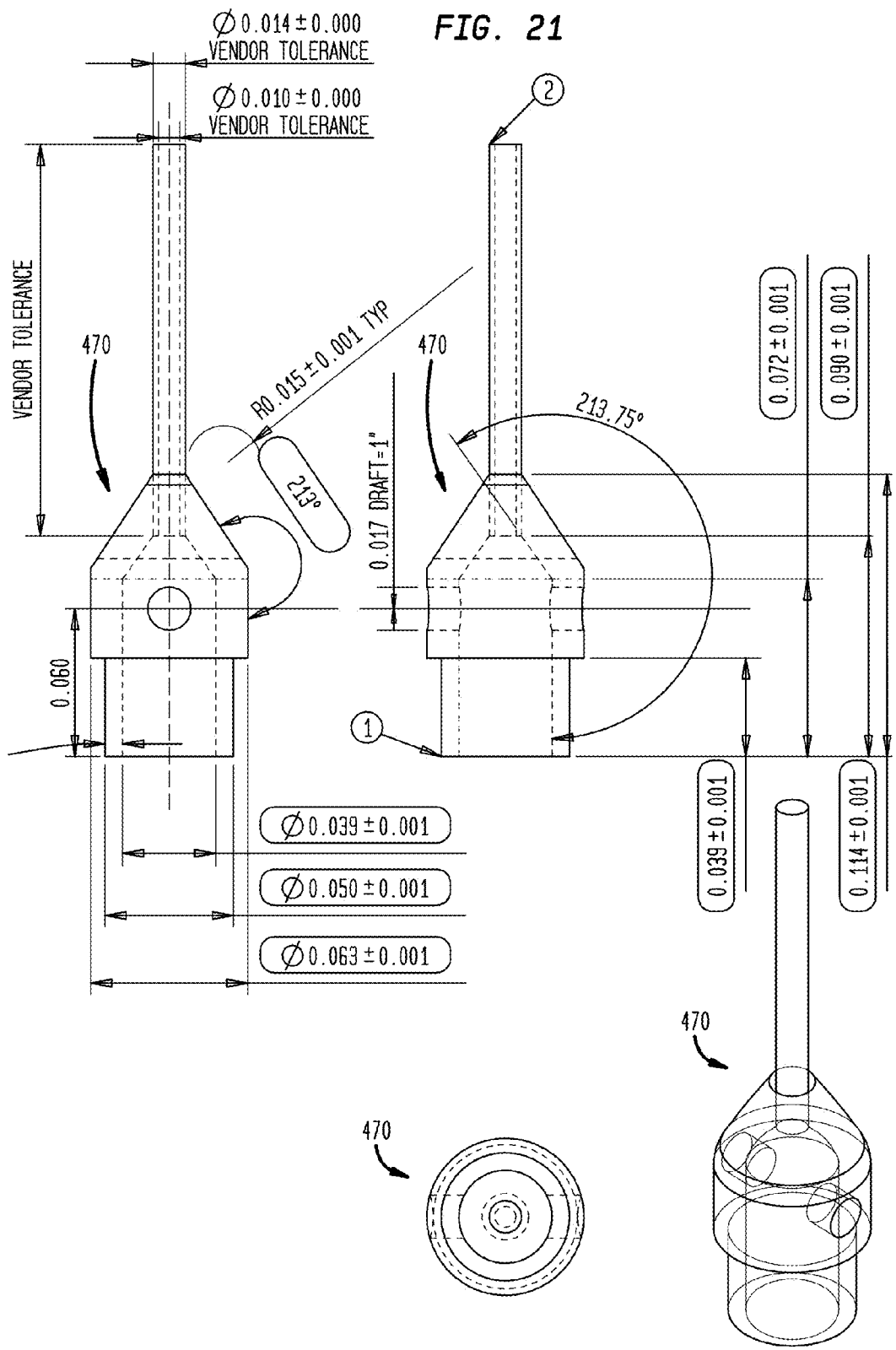
FIG. 21 is a scale drawing of an exemplary embodiment of the nose portion of the CED device of FIG. 16.

A scale drawing of an exemplary molded part 470 is shown with representative dimensions in FIG. 21. Any of the nose portions and/or sheaths described herein can be formed to the same or similar external dimensions. Unless otherwise indicated, the dimensions shown in FIG. 21 are specified in inches.

Figure 22:
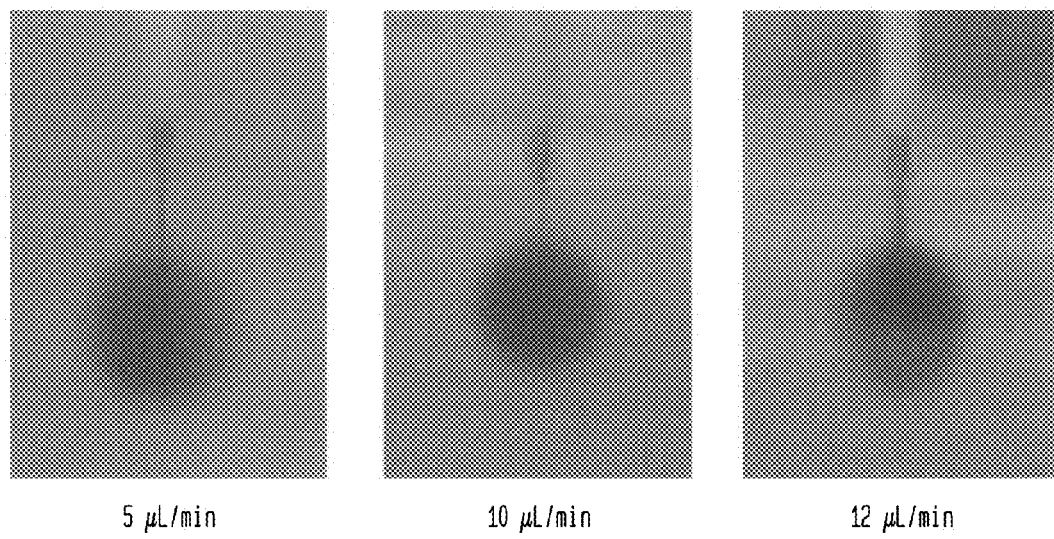
FIG. 22 is a series of images showing infusion of dye using a CED device into a gel designed to simulate tissue.
Figure 23:
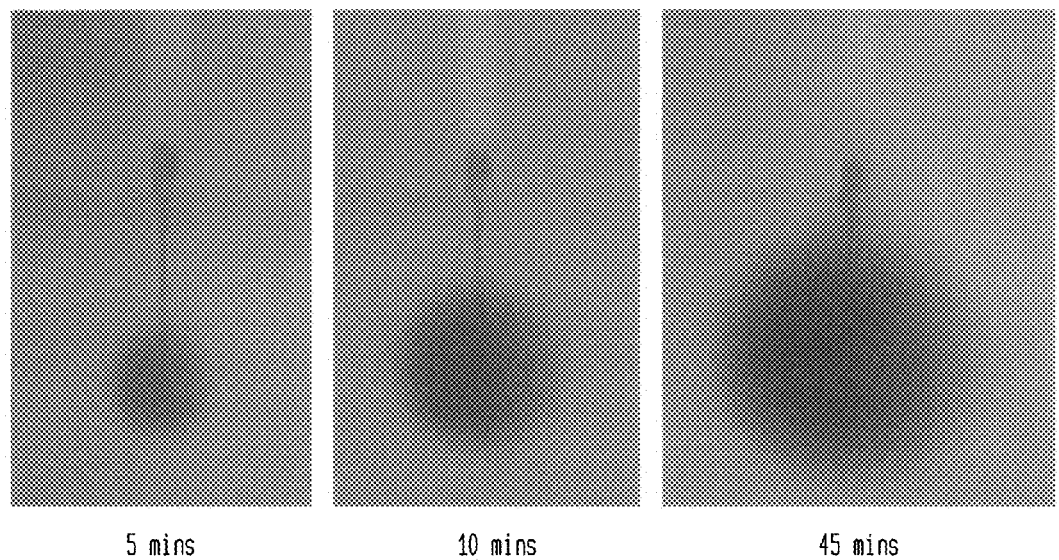
FIG. 23 is another series of images showing infusion of dye using a CED device into a gel designed to simulate tissue.

FIGS. 22-23 illustrate exemplary results of a gel study conducted by infusing dye through a CED device of the type described herein having first and second fluid channels into a gel designed to simulate tissue. As shown in FIG. 22, little or no backflow occurs at flowrates of 5, 10, and 12 μL/min (total flowrate of both channels combined). As shown in FIG. 23, a flowrate of 5 μL/min resulted in a uniform distribution of the dye over time with little or no backflow.

FIGS. 24-29 illustrate exemplary results of an animal study conducted using an in-vivo pig model in which multiple anatomies were infused using CED devices of the type described herein. Little or no backflow along the catheter track was observed at flow rates which are much higher than typical clinical flow rates for CED. The study demonstrated the capability to infuse small, medium, and large molecules using CED devices of the type disclosed herein, and confirmed the functionality of independent flow channels. No blockages or introduction of air bubbles occurred during a multi-hour acute infusion. The device was found to be compatible with magnetic resonance imaging and other stereotactic surgical procedures. No leaks, bond breakages, or other catheter issues were observed.

Figure 24:
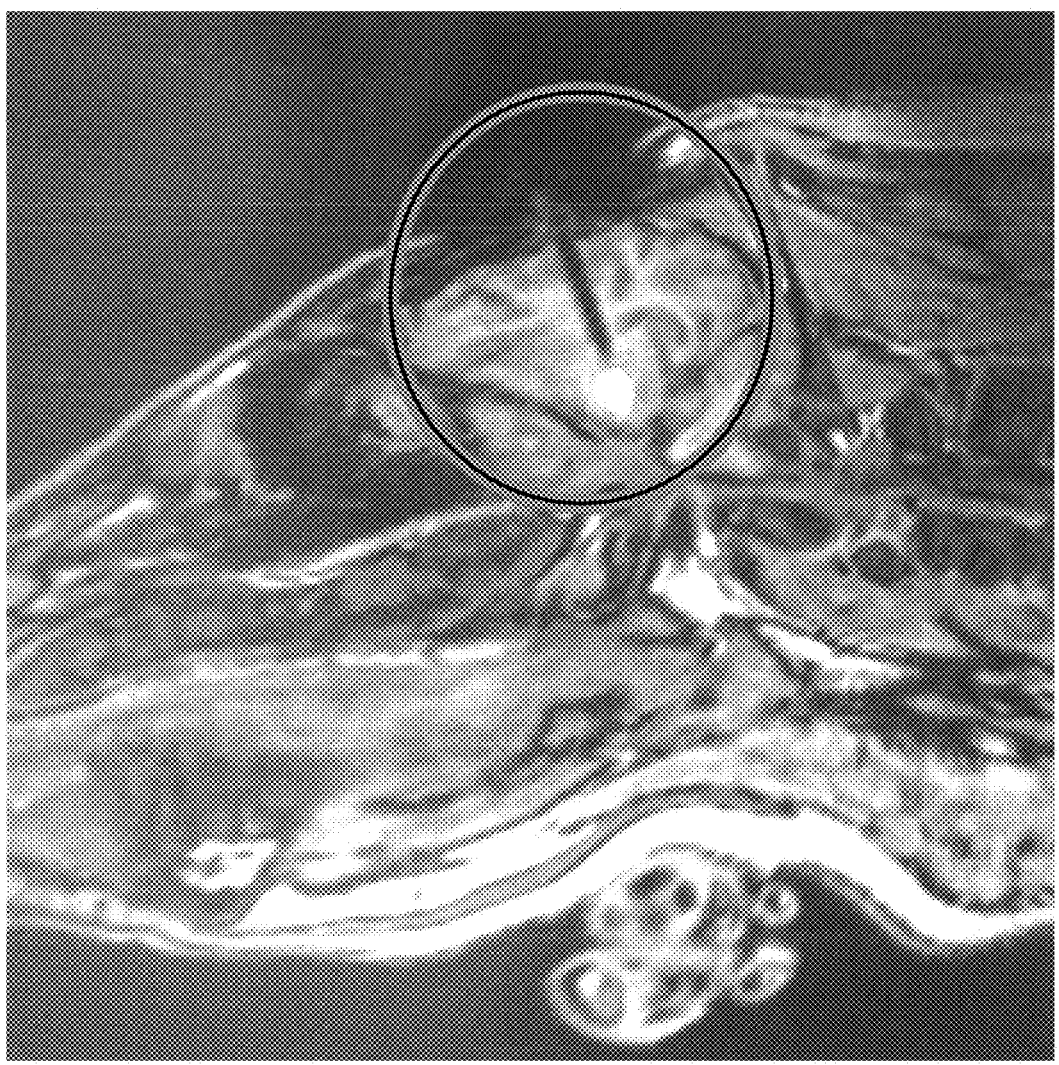
FIG. 24 is a magnetic resonance image of a pig brain in which a CED device is inserted and a gadolinium dye is infused.

As shown in FIG. 24, when inserted into a pig brain, the ceramic catheter body and the bullet nose appear as a thick black line in a magnetic resonance (MR) image. Infused gadolinium (Gd) appears as a bright cloud in the MR image. The micro-tip is not readily visible in the MR image due to its small size.

Figure 25:
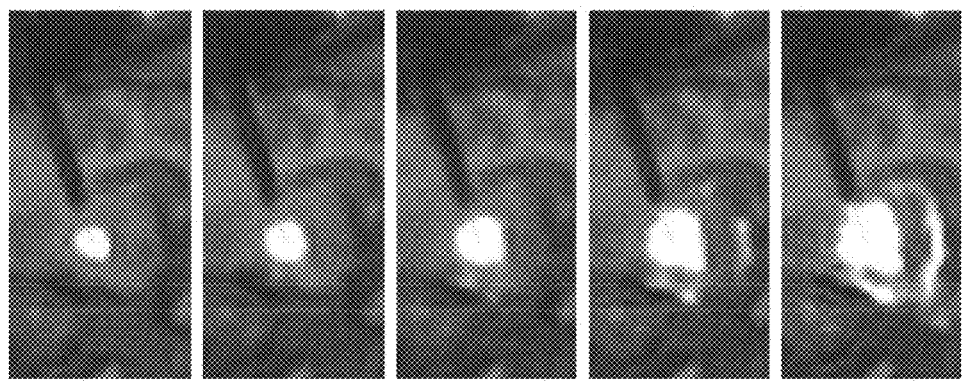
FIG. 25 is a series of magnetic resonance images showing infusion of gadolinium into white matter of a pig's brain at flow rates of 1, 3, 5, 10, and 20 µL/min using a CED device.

FIG. 25 illustrates a series of MR images showing infusion of gadolinium into white matter of a pig's brain at flow rates of 1, 3, 5, 10, and 20 μL/min. As shown, no backflow of infusate occurs along the ceramic catheter shaft track. When the infusion cloud becomes too large, the infusate overflows into surrounding anatomy, rather than flowing back along the catheter track, highlighting the capability for the system to reduce or prevent backflow. While flow rates of up to 20 μL/min are shown, it is expected that similar results would be obtained for flow rates of 30 μL/min or more. These higher flow rates could not be tested during the animal study because the subject brain(s) became saturated with gadolinium.

Figure 26:
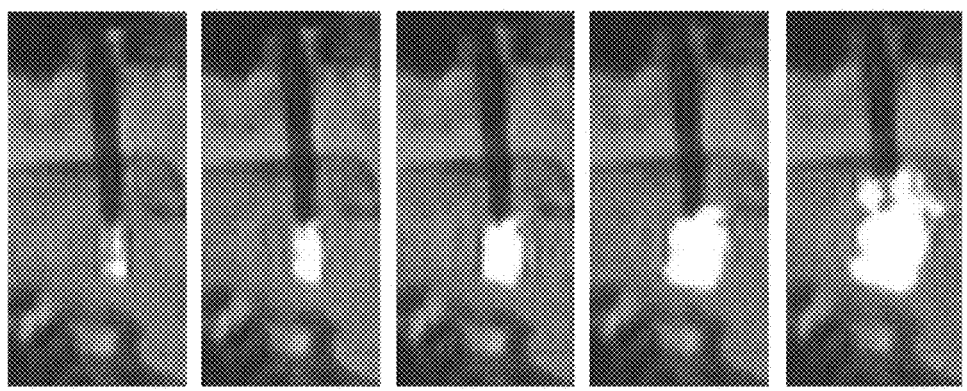
FIG. 26 is a series of magnetic resonance images showing infusion of gadolinium into the thalamus of a pig's brain at flow rates of 1, 3, 5, 10, and 20 µL/min using a CED device.

FIG. 26 illustrates a series of MR images showing infusion of gadolinium into the thalamus of a pig's brain at flow rates of 1, 3, 5, 10, and 20 μL/min. As shown, no backflow of infusate occurs along the ceramic catheter shaft track. While there is slight backflow across the bullet nose at approximately 20 μL/min, this is a flowrate that is significantly higher than typical clinical CED flowrates (generally about 5 μL/min).

Figure 27:
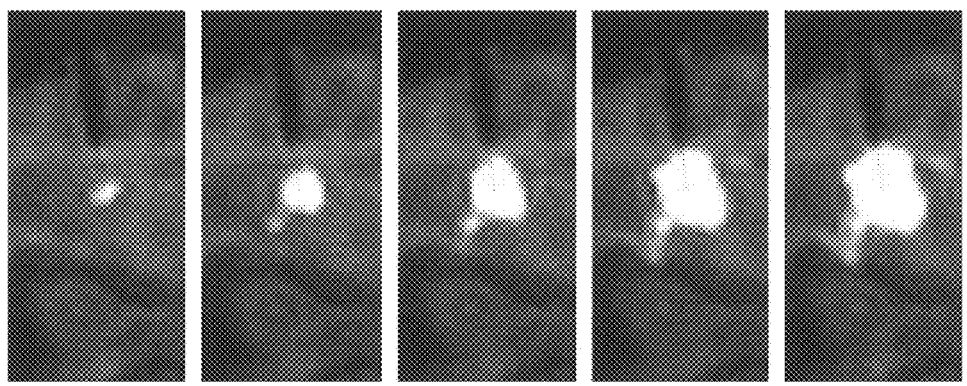
FIG. 27 is a series of magnetic resonance images showing infusion of gadolinium into the putamen of a pig's brain at flow rates of 1, 2, 5, 10, and 15 µL/min using a CED device.

FIG. 27 illustrates a series of MR images showing infusion of gadolinium into the putamen of a pig's brain at flow rates of 1, 2, 5, 10, and 15 μL/min. As shown, no backflow of infusate occurs along the ceramic catheter shaft track as the infusate stays spherical throughout the ramped infusion.

The above-described backflow study showed that there is minimal backflow along the catheter shaft at high flow rates (up to 20 μL/min for white matter, 5-20 μL/min for the thalamus, and 5-15 μL/min for the putamen). These flow rates are much higher than typical clinical CED flow rates (e.g., about 5 μL/min). The determination as to whether backflow occurred was made using a 3D analysis of the infusion, not solely based on the MR images included herein. In a total of eleven infusions conducted in various anatomies, zero incidences of backflow were observed.

Figure 28:
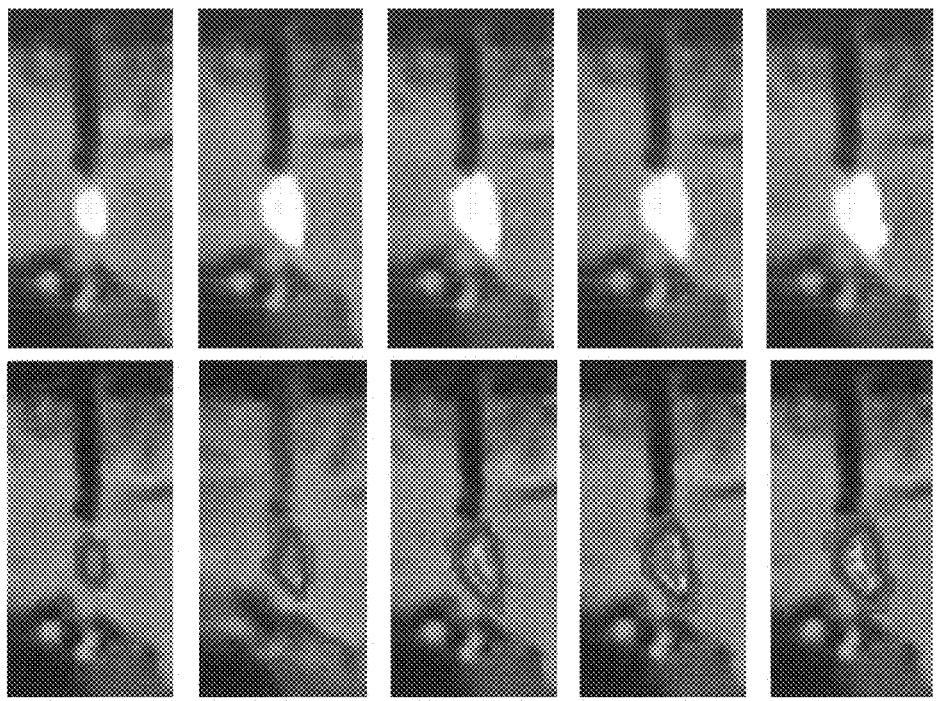
FIG. 28 is a series of magnetic resonance images showing infusion of gadolinium into the white matter of a pig's brain at a flow rate of 5 µL/min using a CED device after infusion periods of 1, 9, 16, 24, and 50 minutes.

FIG. 28 illustrates a series of MR images showing infusion of gadolinium into the white matter of a pig's brain at a flow rate of 5 μL/min after infusion periods of 1, 9, 16, 24, and 50 minutes. The lower set of images includes a distribution overlay. As shown, a uniform distribution with no backflow is observed even for long-duration infusions and when a large volume of infusate is delivered. Similar results were observed in infusions into the thalamus and putamen of the pig's brain.

Figure 29:
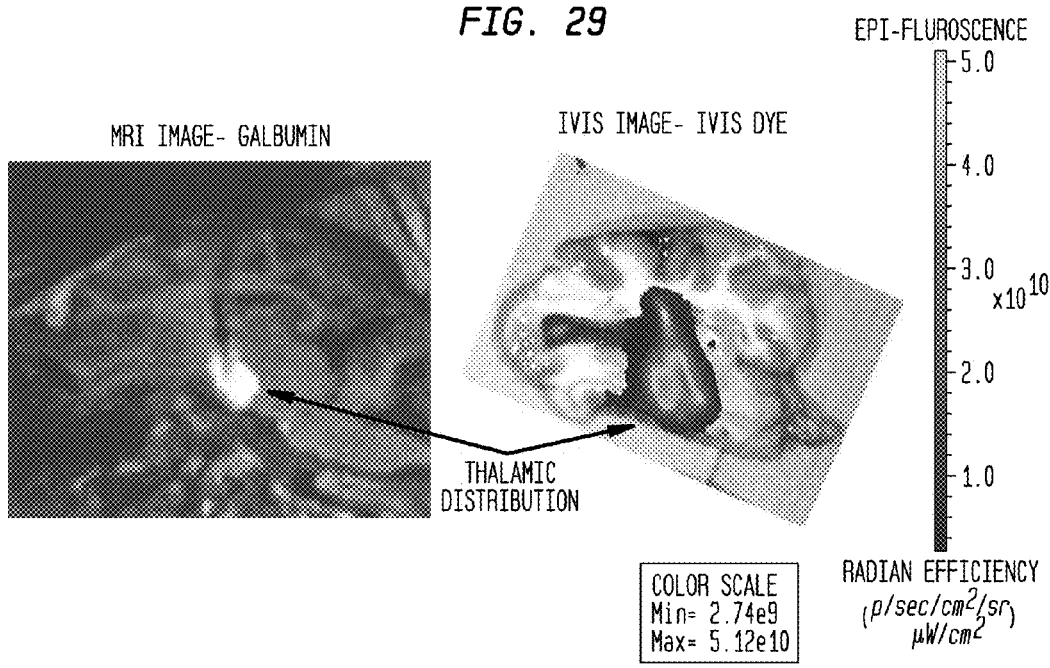
FIG. 29 is a magnetic resonance image and an in vivo imaging system image of the thalamus of a pig's brain when a CED device is used to simultaneously infuse galbumin and IVIS dye.

FIG. 29 illustrates an MR image and an in vivo imaging system (IVIS) image of the thalamus of a pig's brain when a CED device of the type described herein is used to simultaneously infuse galbumin (gadolinium-labeled albumin laced with europium) through a first fluid channel and IVIS dye through a second fluid channel. As shown, the two different infusates were successfully infused from the two independent channels. A uniform distribution of the two infusates indicates mixing at the tip outlet as desired. No evidence of subarachnoid leakage was observed. This demonstrates that the system can be used to deliver Gd tracer and a drug or other molecule while monitoring the Gd tracer under MR to monitor the distribution of the drug or other molecule.

Figure 30:
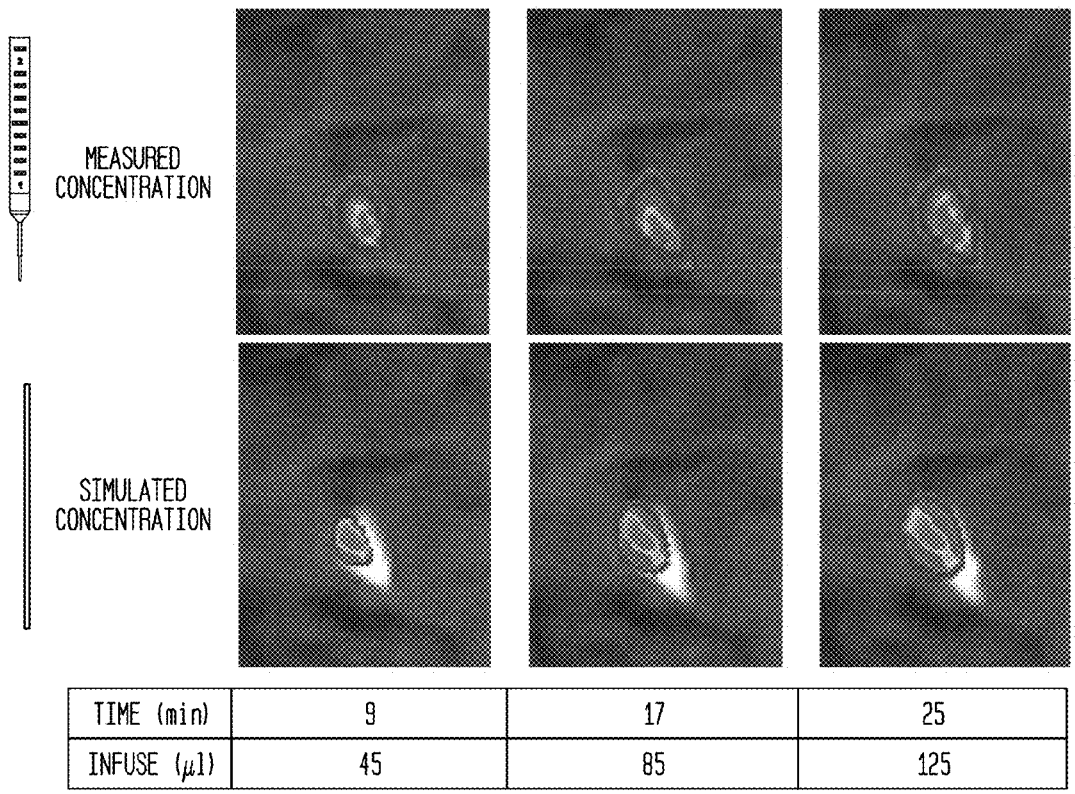
FIG. 30 is a comparison of infusate concentration using a CED device of the type described herein to simulated infusate concentration using a traditional catheter.
Figure 31:
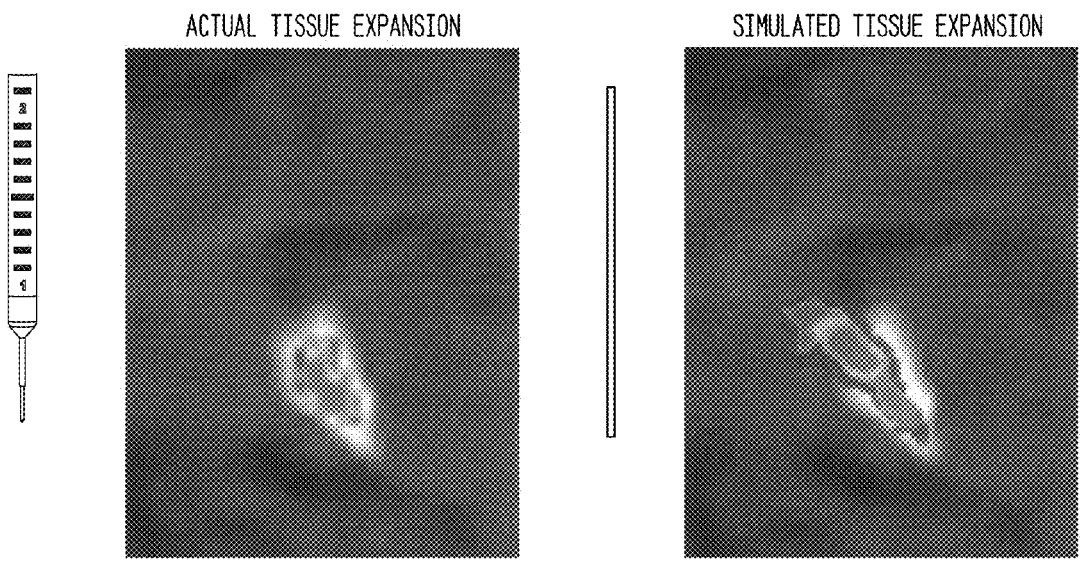
FIG. 31 is a comparison of tissue expansion using a CED device of the type described herein to simulated tissue expansion using a traditional catheter.

FIGS. 30-31 illustrate comparisons between measurements taken with CED devices of the type described herein and simulated measurements for a traditional 0.3 mm catheter. As shown in FIG. 30, CED devices of the type described herein achieve a more uniform concentration of infused colloidal Gd in white matter than traditional 0.3 mm catheters. As shown in FIG. 31, when using CED devices of the type described herein, extracellular expansion of white matter tissue is confined to the tip area by the bullet nose and tube-step, which prevents backflow along the catheter track. With traditional 0.3 mm catheters, on the other hand, increased extracellular expansion occurs along the catheter track due to the infusion pressure and backflow results.

The above-described infusion studies showed that 150 μL of infusate could be delivered into white matter and thalamus with no backflow along the catheter track. It also showed that the concentration profile of infusate distribution in tissue was within typical ranges for intraparenchymal drug delivery. Successful colloidal Gd (large molecule 30-50 nm) infusion was also demonstrated.

The devices disclosed herein can be manufactured using any of a variety of techniques. For example, the devices can be manufactured by assembling lengths of tubing over one another, by micro-machining lengths of tubing, by molding steps or nose features containing tissue-receiving spaces onto a fluid conduit, or by constructing one or more portions of the device on a substrate using a lithographic microfabrication process.

Further details on CED methods and devices, as well as related manufacturing techniques, exemplary micro-tips, and exemplary catheters are disclosed in the following references, the entire contents of each of which are hereby incorporated by reference herein:

U.S. Publication No. 2013/0035560, filed on Aug. 1, 2012, entitled MULTI-DIRECTIONAL MICROFLUIDIC DRUG DELIVERY DEVICE;

U.S. Publication No. 2013/0035574, filed on Aug. 1, 2012, entitled MICROFLUIDIC DRUG DELIVERY DEVICES WITH VENTURI EFFECT;

U.S. Publication No. 2013/0035660, filed on Aug. 1, 2012, entitled MULTIDIRECTIONAL MICROFLUIDIC DRUG DELIVERY DEVICES WITH CONFORMABLE BALLOONS;

U.S. Provisional Application No. 61/835,905, filed on Jun. 17, 2013, entitled METHODS AND DEVICES FOR PROTECTING CATHETER TIPS;

U.S. Provisional Application No. 61/860,402, filed on Jul. 31, 2013, entitled DRUG DELIVERY SYSTEMS;

U.S. Publication No. 2010/0098767, filed on Jul. 31, 2009, entitled CONVECTION ENHANCED DELIVERY APPARATUS, METHOD, AND APPLICATION; and U.S. Publication No. 2013/0046230, filed on Nov. 7, 2012, entitled ULTRASOUND-ASSISTED CONVECTION

ENHANCED DELIVERY OF COMPOUNDS IN VIVO WITH A TRANSDUCER CANNULA ASSEMBLY.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A convection-enhanced-delivery (CED) device, comprising:
    a micro-tip having a proximal portion comprising first and second legs, a central portion, a distal portion, a first fluid channel extending along the first leg of the proximal portion, the central portion, and the distal portions, and a second fluid channel extending along the second leg of the proximal portion, the central portion, and the distal portion, the first and second fluid channels each having an outlet port at a distal end thereof and an inlet port at a proximal end thereof;
    a first outer sheath disposed coaxially over the distal portion of the micro-tip such that the distal portion of the micro-tip protrudes from a distal end of the first outer sheath;
    a first tissue-receiving space defined between an exterior surface of the micro-tip and an interior surface of the distal end of the first outer sheath;
    a catheter body extending proximally from the micro-tip such that the first and second fluid channels of the micro-tip are in fluid communication with respective first and second inner lumens of the catheter body; and
    a nose portion disposed over at least the central portion of the micro-tip and extending between the first outer sheath and the catheter body such that the nose portion defines an exterior surface that tapers from a reduced distal diameter corresponding to the outside diameter of the first outer sheath to an enlarged proximal diameter corresponding to the outside diameter of the catheter body.

2. The device of claim 1, wherein the tissue-receiving space is configured to compress tissue received therein as the device is advanced through the tissue.

3. The device of claim 2, wherein tissue compressed by the tissue-receiving space forms a seal that reduces proximal backflow of fluid ejected from at least one of the outlet ports beyond the tissue-receiving space.

4. The device of claim 1, further comprising a second outer sheath disposed over the first outer sheath such that a second tissue-receiving space is defined between an exterior surface of the first outer sheath and an interior surface of a distal end of the second outer sheath.

5. The device of claim 1, wherein the interior surface of the distal end of the first outer sheath is shaped to compress tissue received therein as the device is advanced through the tissue.

6. The device of claim 5, wherein the interior surface of the distal end of the first outer sheath is conical.

7. The device of claim 5, wherein the interior surface of the distal end of the first outer sheath is convex.

8. The device of claim 5, wherein the interior surface of the distal end of the first outer sheath is concave.

9. The device of claim 1, wherein an inside diameter of the distal end of the first outer sheath is about 1 μm to about 200 μm greater than an outside diameter of the distal portion of the micro-tip.

10. The device of claim 1, wherein an inside diameter of the distal end of the first outer sheath is about 10 percent to about 100 percent greater than an outside diameter of the distal portion of the micro-tip.

11. The device of claim 1, wherein the first outer sheath has a circular outside cross-section.

12. The device of claim 1, wherein the first and second fluid channels are formed from at least one of a parylene composition, a silastic composition, a polyurethane composition, and a PTFE composition.

13. The device of claim 1, further comprising a fluid reservoir in fluid communication with at least one of the first and second inner lumens of the catheter body and configured to supply a fluid thereto under positive pressure.

14. The device of claim 1, wherein the micro-tip is flexible.

15. The device of claim 1, wherein the micro-tip includes an embedded microsensor.

16. The device of claim 15, wherein the embedded microsensor comprises at least one of a pressure sensor, a glutamate sensor, a pH sensor, a temperature sensor, an ion concentration sensor, a carbon dioxide sensor, an oxygen sensor, and a lactate sensor.

17. The device of claim 1, wherein the distal end of the micro-tip has an atraumatic shape configured to penetrate tissue without causing trauma.

18. The device of claim 1, wherein the micro-tip contains a quantity of a drug, is coated with a drug, or is impregnated with a drug.

19. The device of claim 18, wherein the drug comprises at least one of an antibacterial agent, an anti-inflammatory agent, a corticosteroid, and dexamethasone.

20. The device of claim 1, wherein the micro-tip comprises a substrate having the first and second fluid channels formed thereon.

21. The device of claim 20, wherein the substrate has a rectangular transverse cross-section.

22. The device of claim 1, wherein the catheter body is formed from a rigid material and the first and second inner lumens of the catheter body are defined by first and second sleeves formed from a flexible material.

23. The device of claim 22, wherein the catheter body is formed from at least one of ceramic, PEEK, and polyurethane and wherein each sleeve is formed from at least one of polyimide, pebax, PEEK, polyurethane, silicone, and fused silica.

24. The device of claim 1, wherein the catheter body is formed from a flexible material.

25. The device of claim 1, wherein the first and second legs of the micro-tip are received within the first and second inner lumens of the catheter body.

26. The device of claim 1, wherein a proximal end of the nose portion is received within a cylindrical recess defined in a distal end of the catheter body.

27. A method of assembling the device of claim 1, comprising:
    forming the nose portion by molding the nose portion over the first outer sheath;
    inserting the micro-tip into a proximal end of the nose portion;
    coupling the proximal portion of the micro-tip to the catheter body; and
    injecting a flowable material through an inlet port formed in the nose portion to fill the interior of the nose portion and secure the micro-tip and catheter body to the nose portion.

* * * * *